US006027883A

United States Patent [19]
Herrnstadt et al.

[11] Patent Number: 6,027,883
[45] Date of Patent: *Feb. 22, 2000

[54] OPTIMAL PROCEDURE FOR ISOLATION OF MUTANT MITOCHONDRIAL ALLELES

[75] Inventors: Corinna Herrnstadt; Soumitra Ghosh; Eoin D. Fahy; Robert E. Davis, all of San Diego, Calif.

[73] Assignee: Mitokor, San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/757,438

[22] Filed: Nov. 27, 1996

Related U.S. Application Data

[63] Continuation-in-part of application No. 08/536,036, Sep. 29, 1995, abandoned, which is a continuation-in-part of application No. 08/397,808, Mar. 3, 1995, which is a continuation-in-part of application No. 08/219,842, Mar. 30, 1994, Pat. No. 5,565,323.

[51] Int. Cl.[7] ...................................................... C12Q 1/68
[52] U.S. Cl. ............................ 435/6; 435/91.2; 536/25.4; 536/25.41
[58] Field of Search ..................... 435/6, 91.2; 536/23.1, 536/24.3, 24.33, 25.4, 25.41

[56] References Cited

U.S. PATENT DOCUMENTS

| | | | |
|---|---|---|---|
| 5,185,244 | 2/1993 | Wallace | 435/6 |
| 5,192,659 | 3/1993 | Simons et al. | 435/6 |
| 5,565,323 | 10/1996 | Parker et al. | . |

FOREIGN PATENT DOCUMENTS

WO 90/09455  8/1990  WIPO.

OTHER PUBLICATIONS

Parker, Neurology, 1990.
Parker et al. PNAS, 1989.
Suzuki et al. Diabetes Care 17: 1428–32 (abstract cited), 1994.
Parker, et al. "Cytochrome Oxidase Deficiency in Alzheimer's Disease", *Neurology* 40:1302–1303 (1990).
Anderson, et al., "Sequence and Organization of the Human Mitochondrial Genome", *Nature* 290:457–465 (1981).
Bennett, et al., "Cytochrome Oxidase Inhibition A Novel Animal Model of Alzheimer's Disease", *J. of Geriatric Psychiatry and Neurology* 5:93–101 (1992).
Kish, et al., "Brain Cytochrome Oxidase in alzheimer's Disease", *J. of Neurochemistry* 59(2):776–779 (1993).
Bowling, et al., "Age–Dependent Impairment of Mitochondrial Function in Primate Brain", *J. of Neurochemistry* 60(5):1964–1967 (1993).
Chandrasekaran, et al., "Localization of Cytochrome Oxidase (COX) Activity and COX mRNA in Perirhinal and Superior Temporal Sulci of The Monkey Brain", *Brain Research* 606:213–219 (1993).
Wallace, et al., "Mitochondrial DNA Mutations in Epilepsy and Neurological Disease", *Epilepsia* 35(1):S43–S50 (1994).
Shoffner, et al., "Mitochondrial DNA Variants Observed in Alzheimer Disease and Parkinson Disease Patients", *Genomics* 17:171–184 (1993).
Simonian, et al., "Functional Alterations in Alzheimer's Disease: Diminution of Cytochrome Oxidase in the Hippocampal Formation", *J. of Neuropathy and Experimental Neurology* 52(6):580–585 (1993).
Howell, et al., "Leber Hereditary Optic Neuropathy: Identification of The Same Mitochondrial ND1 Mutation in Six Pedigrees", *Am. J. Hum. Genet.* 49:939–950 (1991).
Chandrasekaran, et al., "Differential Expression of Cytochrome Oxidase (COX) Genes in Different Regions of Monkey Brain" *J. of Neuroscience Research* 32:415–423 (1992).
Suggs, et al., "Use of Synthetic Oligonucleotides as Hybridization Probes: Isolation of Cloned cDNA Sequences for Human $\beta_2$–microglobulin", *Proc. Natl. Acad. Sci. USA* 78(11):6613–6617 (1981).
Saiki, et al., "Genetic Analysis of Amplified DNA with Immobilized Sequence–Specific Oligonucleotide Probes", *Proc. Natl. Acad. USA* 86:6230–6234 (1989).
Kuppuswamy, et al., "Single Nucleotide Primer Extension to Detect Genetic Diseases: Experimental Application to Hemophilia B (Factor IX) and Cystic Fibrosis Genes", *Proc. Natl. Acad. Sci. USA* 88:1143–1147 (1991).
Syvanen, et al., "A Primer–guided Nucleotide Incorporation Assay in The Genotyping of Apolipoprotein E" *Genomics* 8:684–692 (1990).
Landegren, et al., "A Ligase–mediated Gene Detection Technique", *Science* 241:1077–1080 (1988).
Conner, et al., "Detection of Sickle Cell $\beta^s$–globin Allele by Hybridization with Synthetic Oligonucleotides", *Proc. Natl. Acad. Sci. USA* 80:278–282 (1983).
Nickerson, et al., "Automated DNA Diagnostics Using An ELISA–based Oligonucleotide Ligation Assay", *Proc. Natl. Acad. Sci. USA* 87:8923–8927 (1990).
Fodor, et al., "Multiplexed Biochemical Assays with Biological Chips", *Nature* 364:555–556.
Fodor, et al., "Light–directed, Spatially Addressable Parallel Chemical Synthesis" *Research Article* 767–773 (1991).

(List continued on next page.)

*Primary Examiner*—Carla J. Myers
*Attorney, Agent, or Firm*—Seed & Berry LLP

[57] ABSTRACT

A sample preparation procedure for mitochondrial (mt) DNA analysis is described. The present method for isolating mtDNA uses sedimentation techniques for separating erythrocytes from lymphocytes and platelets (crude buffy coat fraction), followed by DNA extraction from the crude buffy coat fraction by boiling in water. This approach improves the yield of mutant DNA, enhancing the sensitivity of subsequent mutation interrogation techniques and allowing for meaningful statistical treatment of the degree of heteroplasmy within the mitochondrial DNA.

23 Claims, 9 Drawing Sheets

OTHER PUBLICATIONS

Matthews and Kricka, "Analytical Strategies for The Use of DNA Probes" *Analytical Biochemistry* 169:1–25 (1988).

Francis Barany, "Genetic Disease Detection and DNA Amplification Using Cloned Thermostable Ligase", *Proc. Natl. Acad. Sci. USA* 88:189–193 (1991).

Gibbs, et al., "Detection of Single DNA Base Differences by Competitive Oligonucleotide Priming", *Nucleic Acids Research* 17(7):2437–2448 (1989).

Ghosh, et al., "Use of Maleimide–thiol Coupling Chemistry for Efficient Syntheses of Oligonucleotide–enzyme Conjugate Hybridization Probes", *Bioconjugate Chem.* 1(1)71–76 (1990).

Ishii and Ghosh, "Bead–based Sandwich Hybridization Characteristics of Oligonucleotide–Alkaline Phosphatase Conjugates and Their Potential for Quantitating Target RNA Sequences", *Bioconjugate Chem.* 4(1):34–41 (1993).

Jablonski, et al., "Preparation of Oligodeoxynucleotide–alkaline Phosphatase Conjugates and Their Use as Hybridization Probes", *Nucleic Acids Research* 14(15):6115–6129 (1986).

Li, et al., "Enzyme–linked Synthetic Oligonucleotide Probes: Non–Radioactive Detection of Enterotoxigenic *Escherichia Coli* in Faecal Specimens", *Nucleic Acids Research* 15(13);5275–5287 (1987).

Newton, et al., "Analysis of Any Point Mutation in DNA. The Amplification Refractory Mutation System (ARMS)", *Nucleic Acids Research* 17(7):2503–2517 (1989).

Gingeras, et al., "Use of Self–sustained Sequence Replication Amplification Reaction to Analyze and Detect Mutations in Zidovudine–resistant Human Immunodeficiency Virus", *J. of Infectious Diseases* 164:1066–1074 (1991).

Erlich, et al., "Specific DNA Amplification", *Nature* 331:461–462 (1988).

Richman, et al., "Human Immunodeficiency Virus Type 1 Mutants Resistant to Nonnucleotide Inhibitors of Reverse Transcriptase Arise in Tissue Culture", *Proc. Natl. Acad. Sci. USA* 88:11241–11245 (1991).

Wu and Wallace, "The Ligation Amplification Reaction (LAR)–amplification of Specific DNA Sequences Using Sequential Rounds of Template–dependent Ligation", *Genomics* 4:560–569 (1989).

Barany, et al., *PCR Methods and App.* 1:5–16 (1991).

Marzuki, et al., *Hum. Genet.* 88:139–145 (1991).

Wallace, D.C., *Science* 256:628–632 (1992).

Partridge, et al., *Arch. Biochem. Biophys.* 310:210–217 (1994).

Parker, Davis *Ann. Neurol.* 26:719–723 (1989).

Jenner, P. *Acta Neurol. Scand.* 84:6–15 (1991).

Hutchin, et al., *Proc. Natl. Acad. Sci.* 92:6892–6895 (1995).

Picketts, D.J., et al., *Hum. Genet.* 89:155–157 (1992).

Livak, K.J., et al. *Hum. Mutation* 3:379–385 (1994).

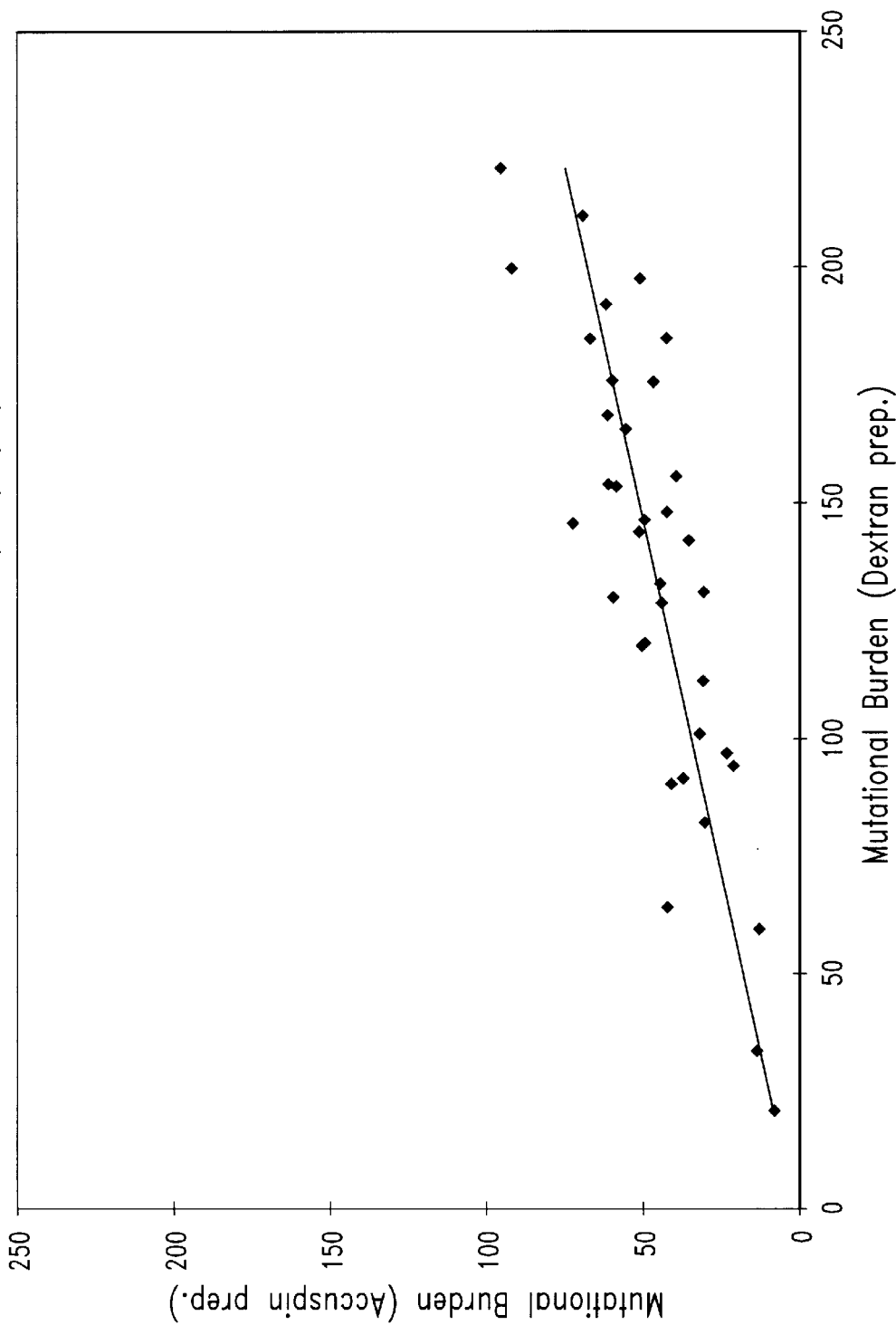

OPTIMAL PROCEDURE FOR ISOLATION OF MUTANT MITOCHONDRIAL ALLELES

This application is a continuation-in-part of U.S. application Ser. No. 08/536,036, filed Sep. 29, 1995, for OPTIMAL PROCEDURE FOR ISOLATION OF MUTATIONAL MITOCHONDRIAL ALLELES, now abandoned, which is a continuation-in-part of U.S. application Ser. No. 08/397,808, filed Mar. 3, 1995 for CELLULAR AND ANIMAL MODELS FOR DISEASES ASSOCIATED WITH MITOCHONDRIAL DEFECTS, which is a continuation-in-part of U.S. application Ser. No. 08/219,842, now U.S. Pat. No. 5,565,323 filed Mar. 30, 1994 for DIAGNOSTIC AND THERAPEUTIC COMPOSITIONS FOR ALZHEIMER'S DISEASE, each of which is incorporated herein by reference in its entirety.

BACKGROUND OF THE INVENTION

An important feature of any nucleic acid-based diagnostic assay is the sample preparation method for extracting DNA or RNA from blood, cells or target tissue. A critical requirement of this first step is to obtain a target nucleic acid of sufficient purity and quantity that is suitable for subsequent processes such as amplification or hybridization. Many techniques and methods have been described in the literature for the purpose of isolating nucleic acids. Typically, methods used to obtain DNA utilize detergent action or mechanical treatment for disruption of cells, followed by enzymatic digestion of the protein contaminants with proteases such as Pronase and Proteinase K (see, e.g., *Molecular Cloning: A Laboratory Manual*, Sambrook, J., Fritsch, E. F. and Maniatis, T. Eds., Cold Spring Harbor Press, 1989). The nucleic acids are then purified by organic extraction with phenol/chloroform, followed by ethanol precipitation of the DNA from the aqueous phase. Other methods of DNA extraction from various tissue sources involve the use of chaotropic salts such as guanidinium isothiocyanate and guanidine hydrochloride—reagents which lyse cells rapidly and are strong denaturants.

Adaptations of the basic approaches outlined above are commonly used for DNA isolation from blood. In a simplification of these procedures, DNA can be obtained from small volumes of blood (~50 µL) by boiling in water in the presence of chelating agents such as Chelex-100 (Bio-Rad Laboratories, Richmond Calif.) and used in PCR reactions (see, e.g., Winberg, G., *PCR Methods and Application*, 1, 72–74, 1991).

SUMMARY OF THE INVENTION

The present inventors have modified existing procedures of sample preparation for mitochondrial (mt) DNA analysis. The approach of the present invention uses sedimentation techniques for separating erythrocytes from lymphocytes and platelets (buffy coat fraction), and the DNA is extracted from the buffy coat fraction by boiling in water. This approach improves the sensitivity of subsequent mutation interrogation techniques, allowing for meaningful statistical treatment of the degree of heteroplasmy within the mitochondrial DNA for the diagnosis of mitochondria-associated disease.

According to an embodiment of the present invention, a buffy coat fraction from a whole blood sample is boiled in water to extract cellular DNA. The extracted cellular DNA is then interrogated for mutations at one or more loci known to correlate with mitochondria-associated disease. In one embodiment of the invention, the extracted cellular DNA is interrogated to determine the presence of mutations at one or more loci known to correlate with Alzheimer's disease (AD). Mutations that correlate with the presence or risk of AD include mutations at one or more of COX1, codon 155, COX1, codon 194, COX1, codon 415, COXII, codon 22, COXII, codon 95 and COX II, codon 146. Using this technique, the degree of heteroplasmy at said one or more loci can be quantitated, and Fisher scores reflective of the over-all mutational burden can be calculated for a statistical population. By comparing said Fisher scores to a predetermined threshold, a meaningful diagnosis can be made.

In a second embodiment of the invention, the extracted cellular DNA is analyzed to determine the presence of mutations in the genes for ATP synthase subunit 8 and tRNA lysine which correlate with late onset diabetes mellitus (NIDDM). Five mutations in the tRNA gene and 32 mutations in the gene for ATP synthase subunit 8 correlate with NIDDM in that the mutational burden for each of the mutated sites is elevated in NIDDM.

One advantage of this technique is that it quite unexpectedly increases the proportion of mutant to normal mitochondrial alleles observed with conventional DNA extraction methods. In comparison, analysis of DNA obtained by commonly used extraction procedures that utilize protease treatment and organic extraction show predominantly normal mtDNA.

BRIEF DESCRIPTION OF THE DRAWINGS

FIG. 5 illustrates total mutational burden for two buffy-coat separation procedures.

DETAILED DESCRIPTION OF THE INVENTION

Figure 1:
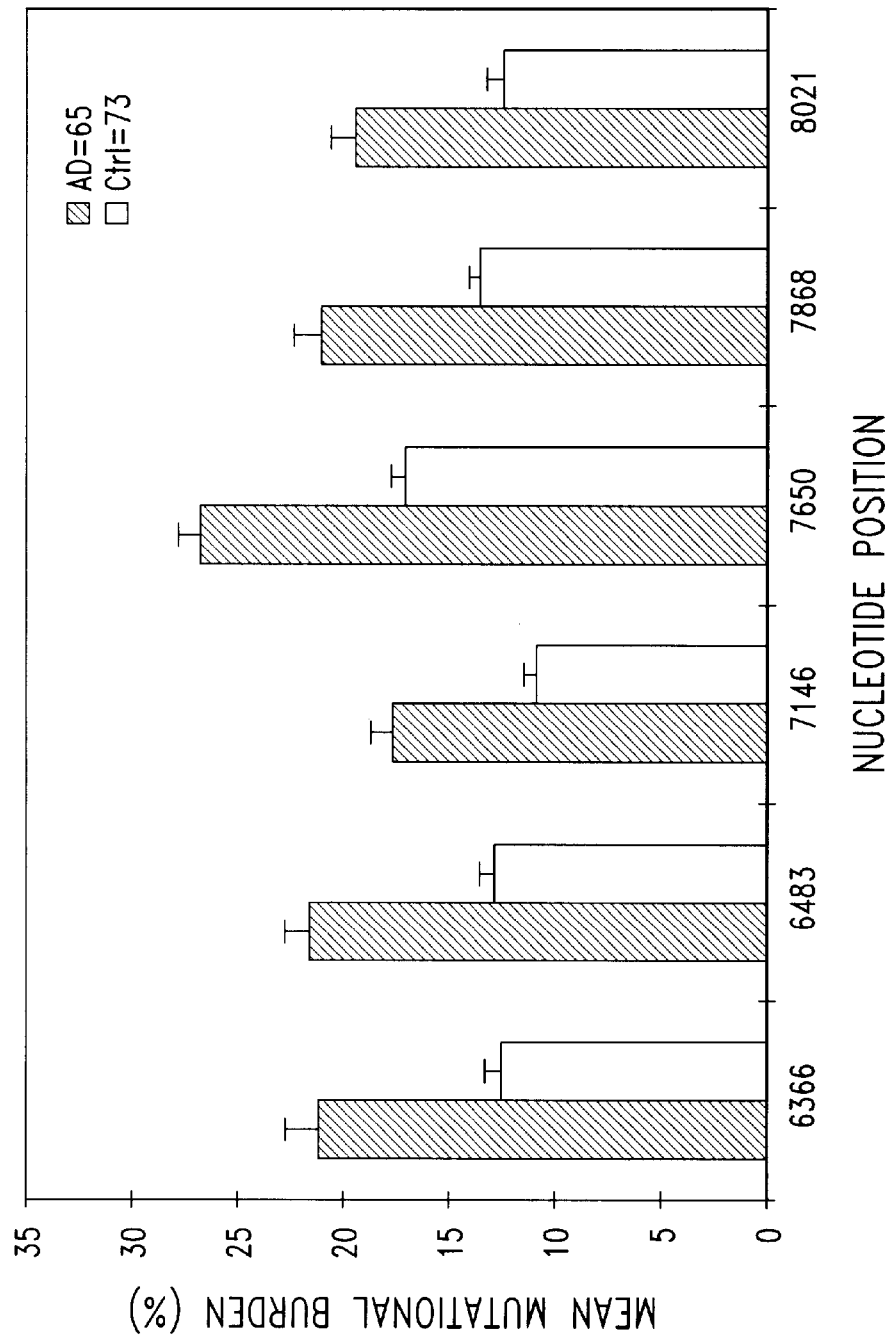
FIG. 1 illustrates the heteroplasmic allelic variation in cytochrome c oxidase subunit 1 and 2 genes in AD patients and controls.

Each cell can contain hundreds of mitochondria and each mitochondria generally contains multiple copies of the mitochondrial genome. Mitochondria are the only known source of extranuclear DNA in humans. Mitochondria DNA encodes exclusively for a number of critical proteins of the electron transport chain, a system loctated within the mitochondria that generates energy for most organs, including the central nervous system, striated muscle and pancreatic islets. Mitochondria DNA also encodes the rRNAs and tRNAs necessary for the expression of other genes present on mitochondrial DNA.

Mitochondrial DNA (mtDNA) mutations recently have been correlated with different sporadic degenerative diseases. Mitochondrial diseases result in defects of oxidative phosphorylation, i.e., conversion of oxygen to cellular energy, and affected cells can no longer generate enough energy to drive normal biochemical functions. Cell death results when the overall oxidative phosphorylation falls below the cellular energetic threshold (Wallace, D. C. (1994) Proc. Natl. Acad. Sci. USA, 91:8739–8746).

Cells can harbor mixtures of mutant and normal mitochondrial DNA (heteroplasmy). During germ-line cell division (meiosis), mutant and normal mitochondria are randomly segregated into daughter cells. Random segregation of mitochondria during meiosis assures that the proportion of mutant to normal mitochondria within a daughter cell will vary. Because the severity of mitochondrial disease is a product of the nature of the mtDNA mutation, i.e., not all mutations have a similar impact on function, and the proportion of mutant mitochondria in a cell, random segregation of mtDNA causes mitochondrial diseases to appear sporadically in families with variable phenotypes. Offspring derived from a daughter cell acquiring a predominance of normal mitochondria will not express the disease, whereas offspring derived from a daughter cell acquiring a predominance of mutant mitochondria will be severely affected. Gradations between these two extremes are also expected. Thus, random segregation of mitochondria during meiosis can explain variable expression of mitochondrial diseases within families.

The heteroplasmy associated with the mitochondrial genome poses a major challenge in the application of DNA-based diagnostic tests for mitochondria-associated diseases. In applying DNA-based diagnostic tests for mitochondria-associated disease, it is essential that the entire heteroplasmic population of mutant and wild-type mtDNA be quantitatively represented. The present inventors have discovered that mutant mtDNA is selectively lost during extraction of cellular DNA from white blood cells by conventional techniques, such as, proteinase K/SDS digestion and phenol/chloroform extraction. A heteroplasmic mtDNA population treated by such technique yields mostly wildtype DNA, mutant mtDNA having been lost in the extraction procedure. Thus, there is a need in the field for an improved mtDNA extraction procedure that provides a quantitative yield of mutant and wild-type mtDNA.

95% of all cases of AD are not attributable to nuclear chromosomal abnormalities. This type of AD has a late age of onset (after the age of 60) and is commonly referred to as sporadic AD. First degree relatives of affected probands, however, have an increased risk of AD, suggesting an unknown genetic contribution to this disease.

Recent epidemiological studies indicate that individuals with a maternal relative affected with AD are at higher risk than the general population. This suggests a maternally derived genetic factor and implicates the mitochondrial genome which is solely inherited from the mother. Sporadic inheritance with familial association, maternal transmission, delayed age of onset and variable phenotypic expression, as seen in AD, are hallmarks of mitochondrial disease.

Our research has implicated a genetic lesion encoded by a heteroplasmic allele of a mitochondrial gene in the sporadic appearance of AD (see, e.g., U.S. Ser. No. 08/219,842). We have evaluated electron transport chain (ETC) function in platelet and brain mitochondria from AD patients and identified a specific defect in Complex IV (cytochrome c oxidase) activity (see, e.g., U.S. Ser. No. 08/397,808). We further demonstrated that Complex IV protein complex is present in normal concentrations but is kinetically perturbed in AD brain. These factors suggest an abnormally constructed enzyme complex, arising from mutations in the genes encoding critical components of Complex IV.

Complex IV is composed of 13 subunits; 10 are encoded by the nuclear genome and three by the mitochondrial genome. Using our proprietary cybrid technology, we showed that the focal ETC dysfunction in AD is associated with genetic lesions in the mitochondrial genome. Further genetic analysis revealed heteroplasmic point mutations in the mtDNA encoding for complex IV subunits 1 and 2 (but not 3) in blood of clinical diagnosed AD patients and brains of autopsy-confirmed AD cases.

Six missense mutations, three at nucleotide positions 6366, 6483, 7146 (within codons 155, 194 and 415 of cytochrome c oxidase subunit 1)and three at nucleotide positions 7650, 7868 and 8021 (within cytochrome c oxidase subunit codons 22, 95 and 146) correlate with the presence of Alzheimer's disease, are resident in the same mitochondrial genome and are linked. In general, when one of these mutations appears, the other five mutations also appear. However, rare exceptions do exist; particularly when the 7146 mutation in codon 415 appears as a homoplasmic allele. In the process of improving our ability to detect these mutations, we discovered that most controls (demented, diseased and cognitively normal) also exhibit low levels of each of these six mutations. However, using the present mtDNA extraction procedure and a quantitative, multiplexed, primer extension assay, we have been able to demonstrate quantitative differences in the abundance of mutated alleles at each of these loci between Alzheimer's disease patients and controls.

Improvements in mtDNA extraction using the method of the present invention selectively increase the relative proportion of mutant to normal mitochondrial alleles. The relative abundance of mutant mitochondrial alleles is significantly increased by the present mtDNA extraction procedure, enabling the application of DNA-based diagnostic procedures to determine the presence or risk of mitochondria-associated disease, such as, for example, AD.

Seventy-three controls and sixty-five patients with clinical diagnosis of probable/possible AD were examined. mtDNA was extracted from blood from these individuals by the DNA extraction procedure of the present invention. The percentage of mutant to normal mtDNA was determined for each of the six AD-associated loci by the primer extension assay. The analysis reveals that the six mutations appear at low levels in most controls but are elevated in a significant number of AD cases (Table 11). As a group, AD cases exhibited statistically significant increases at each of the six nucleotide sites relative to age-matched and other disease controls (FIG. 1).

Figure 2:
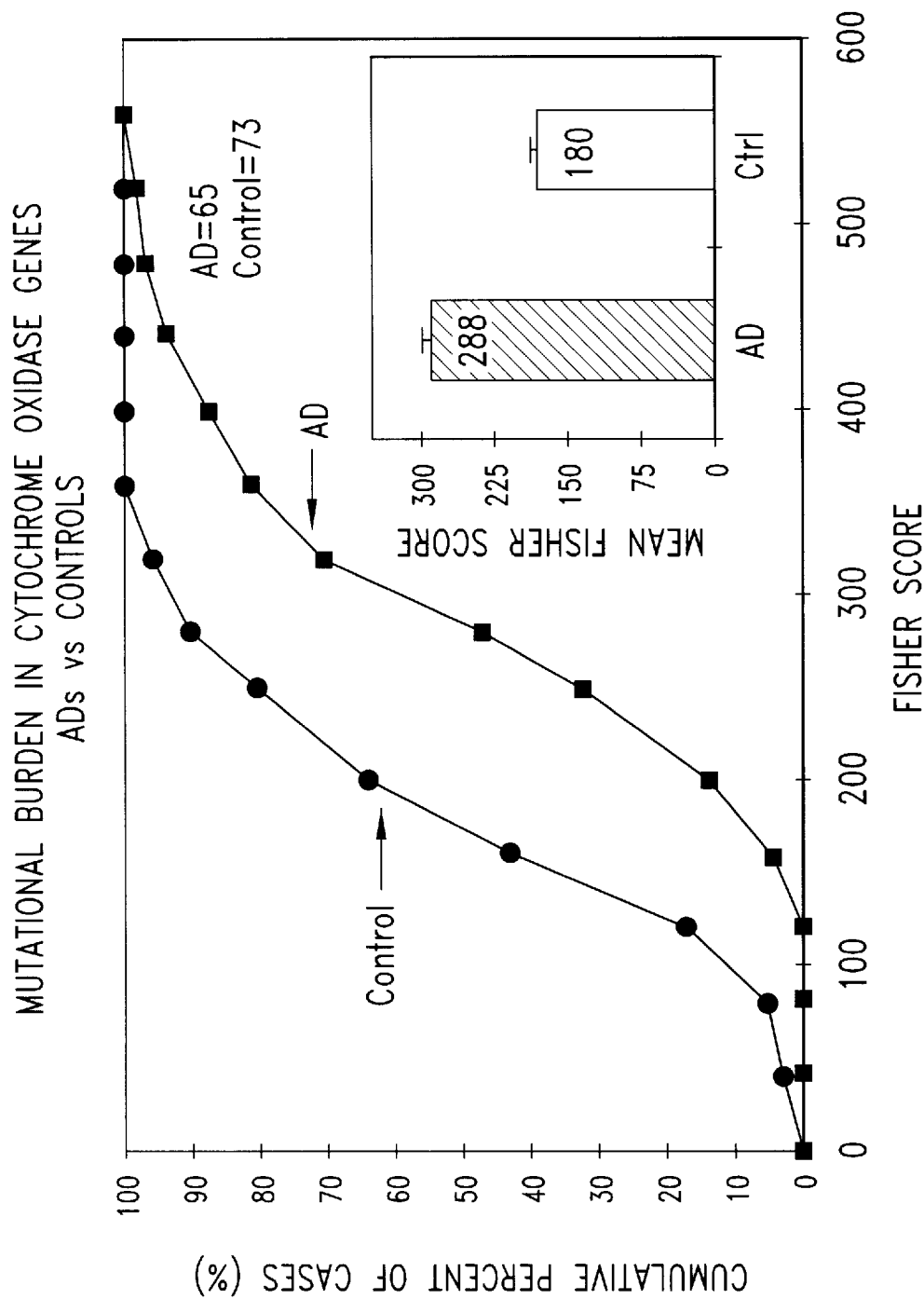
FIG. 2 is a graph showing the mutational burden via Fisher Scores in cytochrome c oxidase genes in AD and control patients.

To estimate the overall mutational burden across these six nucleotide sites, these data were subjected to analysis by the Fisher multivariate discriminant analysis technique (see Johnson, R. and Wichern, D. (1988) In Applied Multivariate Statistical Analysis, Prentice Hall, pp 461–471, Englewood Cliffs, N.J.). The multivariate discriminant analysis technique separates and classifies individuals into distinct populations based on differences in mutational burden. The method yields a univariate observation (Fisher score) that represents the overall mutational burden at each of these nucleotide positions. The higher the Fisher score, the greater the mutational burden, and the higher the Fisher score, the better these six mutations taken together discriminate AD from controls. Taken together, the AD cases have significantly higher Fisher scores (as a consequence of their higher mutational burden) than controls (FIG. 2 inset).

To illustrate the representation of individuals within the population, Fisher scores were used to create a cumulative frequency distribution. As seen in FIG. 2, the control and AD populations are distinctly separated on the basis of the overall mutational burden and the AD-associated nucleotide sites. It is rare for AD cases to have low Fisher scores while it is common for controls to have low scores. Approximately 50% of controls have Fisher scores below 170 while only 5% of the AD cases have Fisher scores below this value. Low Fisher scores, therefore, represent a negative risk factor for AD.

In contrast, it is common for AD cases to have high mutational burdens, and hence, higher Fisher scores. It is very rare for controls to have high Fisher scores. For illustration, approximately 20% of all AD cases have Fisher scores above 350 while no controls exceed this value. An intermediate level can also be defined by the data. Approximately 55% of AD cases have Fisher scores exceeding 270, while only 10% of controls exceed this level of mutational load. High Fisher scores, therefore, represent a strong positive risk factor for AD.

Figure 3:
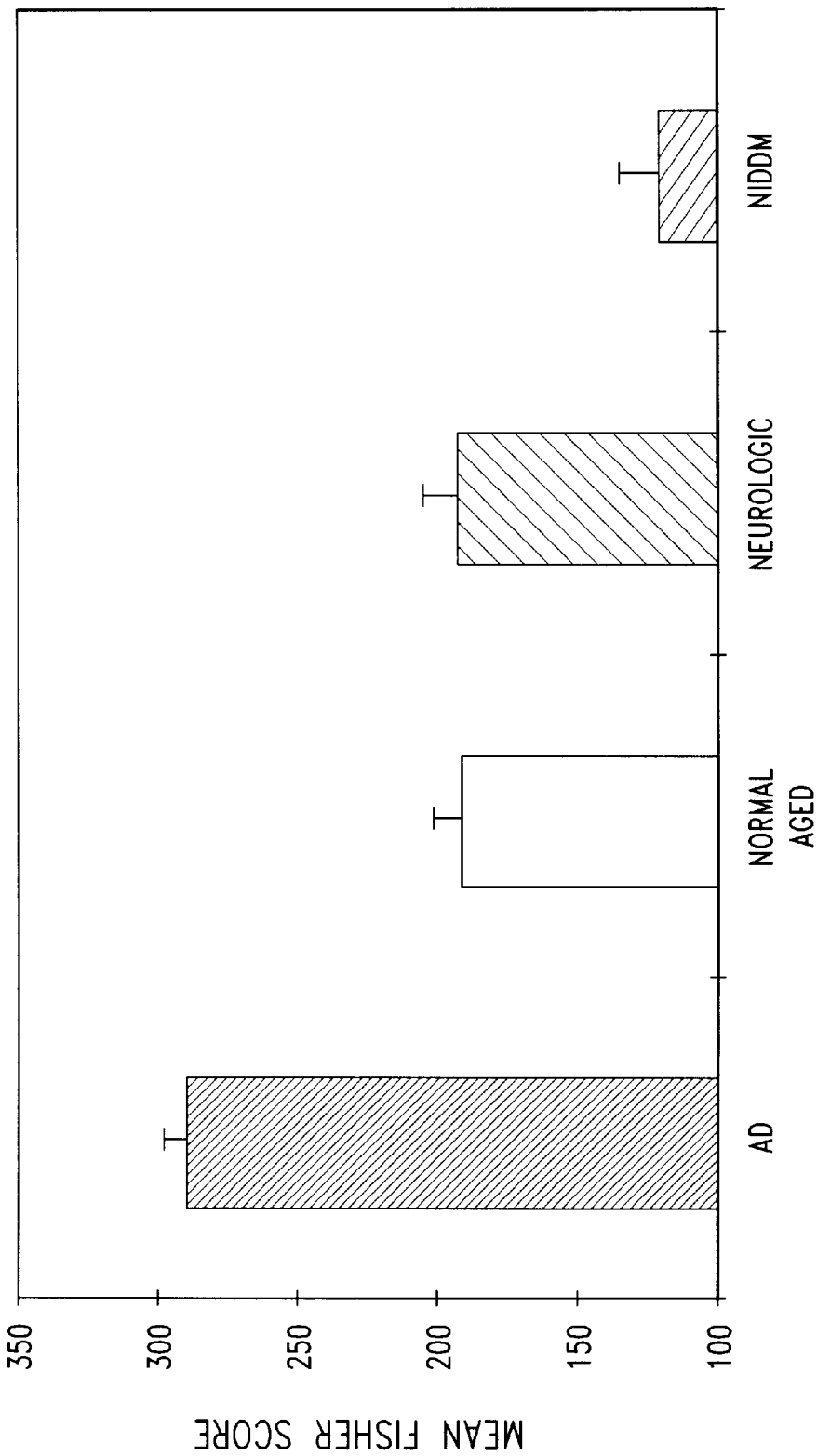
FIG. 3 illustrates the mean mutational burden in cytochrome c oxidase genes in AD and control patients.

High levels of the six AD-associated mutations are relatively specific for AD. Levels of these mutations are not elevated above control values in a variety of neurological patients including Parkinson's disease and in patients with non-insulin dependent diabetes (FIG. 3). Thus, the cytochrome c oxidase genetic lesions segregate specifically with a subtantial portion of AD patients and arises from specific point mutations that define a unique mitochondrial DNA.

The AD cases that do not have elevated levels of these mutations may represent the genetic heterogeneity of AD, and cases mis-diagnosed with AD. One sub-group is senile dementia of the Lewy body variant (SDLBV). SDLBV is clinically indistinguishable from AD but is pathologically distinct and accounts for between 20–30% cases of autopsied AD cases. In autopsied brains of SDLBV cases, the activity of cytochrome c oxidase is normal and these patients are therefore unlikely to carry elevated levels of these mutations. The neuropathology of SDLBV includes senile plaque formation, Lewy bodies (proteinaceous structures) and few or sparse neurofibrillary tangles (NFT). The brains from SDLBV patients have fewer NFTs in the hippocampus, parahippocampal gyrus and frontal cortex compared to AD brains. SDLBV cases also have lower cortical choline acetyltransferase (ChAT) activity than AD cases. ChAT catalyses the synthesis of the neurotransmitter acetylcholine from acetyl CoA and choline, and ChAT deficiencies lead to decreases in levels of acetylcholine. SDLBV is also associated with an increase in the numbers of muscarinic receptors in the neocortex while AD is not. Therefore, SDLBV brains have decreased cholinergic function but increased capacity to respond to acetylcholine because of increased receptor numbers in the neocortex. SDLBV and not AD patients are most likely to respond to cholinergic therapies, e.g., with the drug Cognex. The diagnostic test based on AD-associated mutations in mitochondrial cytochrome c oxidase subunit 1 and 2 genes may be useful in selecting patients for cholinergic replacement therapies by exclusion. By excluding AD patients with high mutational burden from clinical trials with cholinomimetics, the population of responders can be enriched. This would exclude AD patients not likely to respond to the drug and thus limit their exposure to possible toxic side-effects of the compounds.

Initially, this assay is intended to be used to confirm a clinical diagnosis of probable/possible mitochondria-associated disease, such as AD, Parkinson's disease, diabetes, etc., in a particularly preferred embodiment, AD, with only demented patients being examined. Therefore, the consequences of a false positive are reduced and the assay sensitivity should be maximized. Under these circumstances, the theoretical maximal sensitivity of approximately 60% is achieved with approximately 90% specificity using total mutational burden as the endpoint.

Diabetes mellitus is a heterogenous disease with a strong genetic component; monozygotic twins are highly concordant, and first degree relatives from affected individuals show a high incidence of the disease. However, nuclear genes that segregate with diabetes mellitus are known only for rare mutations. Maternal inheritance of the disease suggests mitochondrial involvement.

A rare form of late-onset NIDDM (less than 2% of all cases) associated with nerve deafness was found to segregate with a point mutation in the mitochondrial gene for the tRNA leucine. Individuals carrying this mutation are often diagnosed with insulin dependent diabetes mellitus (IDDM) or insulin deficient non-insulin dependent diabetes mellitus (NIDDM). Mitochondrial DNA (mtDNA) is a 16,659 bp circular molecule which encodes two ribosomal RNAs, 22 tRNAs, and 13 proteins. All 13 proteins are essential components of Complexes I, III, IV and V of the electron transport chain (ETC).

We have evaluated ETC function using our proprietary cybrid technology and determined non-impaired activities for Complexes I and IV. Therefore, the two genes involved with Complex V of the ETC, ATP synthase subunits 6 and 8, were the target for our genetic analysis. Heteroplasmic point mutations in the mtDNA coding for ATP synthase subunit 8 were identified in blood of clinically diagnosed NIDDM patients. Missense mutations which lead to altered protein sequence were identified at nucleotide positions 8396, 8401, 8459, 8463, 8474, 8486, 8487, 8491 and 8508. In addition, five mutations were identified in the tRNA lysine gene at nucleotide positions 8336, 8345, 8348, 8349 and 8351.

DISCUSSION OF THE PREFERRED EMBODIMENTS

According to an embodiment of the present invention, mononuclear cells are first separated from erythrocytes to generate a buffy coat fraction, which is a light colored layer between plasma and red blood cells that contains mostly white blood cells and platelets. Cellular DNA from the buffy coat fraction is then extracted by boiling the cells to achieve cell lysis, followed by centrifugation. The supernatant, which contains the cellular DNA, is then used in subsequent processes, such as amplification followed by mutational analysis.

In summary, it is noted that:
(a) the present procedure results in enrichment of mutant alleles,
(b) the present procedure is not typically used for extraction of DNA, and
(c) no mitochondrial mutations or mitochondrial mutations at very low abundance are seen with the standard procedures involving Proteinase K/phenol/chloroform treatment (these mutations are indeed present and are not artifacts of PCR or primer extension reaction).

The number of mutant alleles appears to be increased in patients suffering from mitochondrial-associated disease. However, since linked mutations in the COXI and COXII genes are commonly observed in both AD patients and in controls, the diagnosis of mitochondrial-associated disease is hampered by the loss of mutant mtDNA during conventional DNA extraction procedures.

The present DNA sample preparation technique provides an increase in the yield of mutant mitochondrial alleles, which correlates with the presence or risk of mitochondria-associated diseases. Thus, the present method enables the quantitation of heteroplasmy observed with mitochondia-associated disease and threshold analysis that permits diagnosis of mitochondria-associated disease, such as, for example, Alzheimer's disease and NIDDM.

THE BOILING PROCEDURE SELECTIVELY INCREASES MUTANT ALLELE FREQUENCIES AT SIX AD-ASSOCIATED LOCI AND FOURTEEN NIDDM-ASSOCIATED LOCI IN mtDNA

Platelets, lymphocytes and other mononuclear cells in whole blood are separated from erythrocytes either by the Accuspin, low speed centrifugation or the Dextran procedures (see Materials and Methods). Cellular DNA from the resulting buffy coat fraction is extracted by two independent methods. In the first method, the cells are lysed by boiling for 10 min, centrifuged, and the DNA in the supernatant is used for subsequent analysis by sequencing or primer extension. The second method involves the commonly used procedure of proteinase K digestion followed by organic extraction (PSPC prep., see Materials and Methods). In a variation of the second method, the crude DNA preparation from the boiling procedure is subjected to limited proteolytic treatment followed by organic extraction (SPP prep., see Materials and Methods).

Cellular DNA obtained by the two extraction procedures are independently analyzed by the primer extension assay and clonal sequencing analysis. In the primer extension assay, the first step involves the use of primer pairs (see Table 1) to generate PCR amplified fragments of the COXI and COXII genes. These fragments encompass the AD-associated mutation sites. The multiplexed primer extension approach described by Fahy and Ghosh (U.S. Ser. No. 08/410,658) is then used to screen for presence of mutations in these PCR-amplified fragments (see Examples and Table 2). In the clonal sequencing approach, the mitochondrial COXI and COXII genes in cellular DNA are PCR amplified as a series of overlapping fragments (see Table 3 for primer pairs). For each fragment, a minimum of four independent PCR reactions are pooled to ensure that replication errors during PCR is diluted sufficiently to avoid being scored as mutations. The PCR fragments are cloned into the vector PCRII, and the blue/white color selection is used to pick out ten clones per fragment for analysis by sequencing (see Examples). The results of the clonal sequencing analysis of cellular DNA isolated from 6 blood samples by the boiling and SPP procedures are shown in Table 4. AD-Associated mutant alleles are detected in all samples isolated by the boiling procedure. The level of heteroplasmy at the six AD-associated codon sites ranges from 10 to 50%. In contrast, except for RI which has a mutation at codon 155 in the COXI gene at 10% frequency, the DNA isolated from the same samples by the SPP procedure is homoplasmic for the wild type allele.

Table 5 shows sequence data for two NIDDM patients, whose DNA was prepared by the Proteinase K/SDS/phenol/ chloroform procedure and the boiling procedure. Each sample was analyzed by sequencing of 10–50 individual clones. Multiple mutations were detected for DNA prepared by the boiling procedure, and almost none for the PSPC procedure. Mutational burden at each specific nucleotide position is indicated as percentage of mutated clones for total quantity of clones sequenced. Five nucleotide positions are monitored in the tRNA Lysine gene. Nine missense mutations (indicated by black bars) and 23 silent mutations are monitored in the ATP Synthase Subunit 8. The mutational frequency for all mutations monitored was 20% to 33% when using the boiling procedure to extract the DNA, whereas the mutational frequency for all mutations monitored was 2.1% to 2.9% when using the PSPC procedure.

TABLE 1

PCR PRIMERS FOR PREPARING PRIMER EXTENTION TEMPLATES

| GENE | SEQUENCE | SENSE | TM | POSITION | LENGTH | PCR LENGTH | PCR RUN TEMP. | CODON ANALYSIS |
|---|---|---|---|---|---|---|---|---|
| COX1 | GAGCCTCCGTAGACCTAACCATCT SEQ. ID NO. 1 | + | 56 | 419 | 24 | 246 | 60° C. | 155, 193, 194 |
| COX1 | GGTCGAAGAAGGTGGTGTTGAG SEQ. ID NO. 2 | − | 55 | 643 | 22 | | 60° C. | |
| COX1 | CCATCATAGGAGGCTTCATTCACTG SEQ. ID NO. 3 | + | 58 | 1163 | 25 | 200 | 60° C. | 415 |
| COX1 | TGATAGGATGTTTCATGTGGTGTATGC SEQ. ID NO. 4 | − | 58 | 1336 | 27 | | 60° C. | |
| COX2 | CATGCAGCGCAAGTAGGTCTACAAGAC SEQ. ID NO. 5 | + | 61 | 7 | 27 | 255 | 60° C. | 28, 68. 74 |
| COX2 | TGTTATGTAAAGGATGCGTAGGGATGG SEQ. ID NO. 6 | − | 60 | 235 | 27 | | 60° C. | |
| COX2 | CCTGCCCGCCATCATCCTAGT SEQ. ID NO. 7 | + | 60 | 201 | 21 | 308 | 60° C. | 90, 95, 110 |
| COX2 | AGCCTAATGTGGGGACAGCTCATG SEQ. ID NO. 8 | − | 60 | 485 | 24 | | 60° C. | 146 |

TABLE 2

PART A
PRIMER AND NUCLEOTIDE COMBINATIONS FOR AD-ASSOCIATED MUTATIONS

LONGER WILD-TYPE PRODUCT

| GENE | MUTATION | PRIMER SEQUENCE | OLIGO# | SENSE | LENGTH | TM | PRODUCTS |
|---|---|---|---|---|---|---|---|
| COX1 | 155 | TGGCCCCTAAGATAGAGGAGA SEQ ID NO:9 | 94–136 | − | 21 | 55 | w23, m22 |
| COX1 | 193 | GACTGGGAGAGATAGGAGAAGTAGG SEQ ID NO:10 | 94–101 | − | 25 | 55 | w28, m26, 27 |
| COX1 | 194 | AGGACTGGGAGAGATAGGAGAAGTA SEQ ID NO:11 | 94–137 | − | 25 | 55 | w28, m26 |
| COX1 | 415 | ACCTACGCCAAAATCCATTTC SEQ ID NO:12 | 94–125 | + | 21 | 55 | w23, m22 |
| COX2 | 22 | TCCCCTATCATAGAAGAGCTTATCA SEQ ID NO:13 | 94–139 | + | 25 | 55 | w28, m26 |

TABLE 2-continued

PART A
PRIMER AND NUCLEOTIDE COMBINATIONS FOR AD-ASSOCIATED MUTATIONS

| COX2 | 68 | GACTAGGATGATGGCGGGCA<br>SEQ ID NO:14 | 94–118 | – | 20 | 60 | w23, m21 |
| --- | --- | --- | --- | --- | --- | --- | --- |
| COX2 | 74 | GGGAGGGCGATGAGGA<br>SEQ ID NO:15 | 94–112 | – | 16 | 55 | w18, m17 |
| COX2 | 90 | CGCATCCTTTACATAACAGACGAG<br>SEQ ID NO:16 | 94–113 | + | 24 | 57 | w26, m25 |
| COX2 | 95(a) | GGCCAATTGATTTGATGGTA<br>SEQ ID NO:17 | 94–114 | – | 20 | 53 | w22, m21, 23 |
| COX2 | 95(b) | GGCCAATTGATTTGATGGTAA<br>SEQ ID NO:18 | 94–155 | – | 21 | 53 | w25, m22 |
| COX2 | 95(c) | GGCCAATTGATTTGATGGTAA<br>SEQ ID NO:18 | 94–155 | – | 21 | 53 | w25, m22 |
| COX2 | 110 | CACCAATGGTACTGAACCTACGAG<br>SEQ ID NO:19 | 94–124 | + | 24 | 57 | w27, m26, 25 |
| COX2 | 146 | ATTATTATACGAATGGGGGCTTCA<br>SEQ ID NO:20 | 94–156 | – | 24 | 57 | w27, m26, 25 |
| COX2 | 146(b) | TTATTATACGAATGGGGGCTTCAA<br>SEQ ID NO:21 | 94–138 | – | 24 | 58 | w26, m25 |

| | | LONGER WILD-TYPE PRODUCT | | | | | | | |
| --- | --- | --- | --- | --- | --- | --- | --- | --- | --- |
| GENE | MUTATION | PRIMER SEQUENCE | dA | dC | dG | dT | ddA | ddC | ddG | ddT |
| COX1 | 155 | TGGCCCCTAAGATAGAGGAGA<br>SEQ ID NO:9 | | X | | | X | | | X |
| COX1 | 193 | GACTGGGAGAGATAGGAGAAGTAGG<br>SEQ ID NO:10 | X | X | | | | | X | X |
| COX1 | 194 | AGGACTGGGAGAGATAGGAGAAGTA<br>SEQ ID NO:11 | | | X | | X | | | |
| COX1 | 415 | ACCTACGCCAAAATCCATTTC<br>SEQ ID NO:12 | X | | | | | X | X | |
| COX2 | 22 | TCCCCTATCATAGAAGAGCTTATCA<br>SEQ ID NO:13 | | X | | | | | | X |
| COX2 | 68 | GACTAGGATGATGGCGGGCA<br>SEQ ID NO:14 | | | X | | X | | | |
| COX2 | 74 | GGGAGGGCGATGAGGA<br>SEQ ID NO:15 | | X | | | | | | X |
| COX2 | 90 | CGCATCCTTTACATAACAGACGAG<br>SEQ ID NO:16 | | | X | | X | | | X |
| COX2 | 95(a) | GGCCAATTGATTTGATGGTA<br>SEQ ID NO:17 | X | | | | | | X | |
| COX2 | 95(b) | GGCCAATTGATTTGATGGTAA<br>SEQ ID NO:18 | | | X | | X | | | X |
| COX2 | 95(c) | GGCCAATTGATTTGATGGTAA<br>SEQ ID NO:18 | | | X | | X | | | |
| COX2 | 110 | CACCAATGGTACTGAACCTACGAG<br>SEQ ID NO:19 | X | | X | | | X | X | |
| COX2 | 146 | ATTATTATACGAATGGGGGCTTCA<br>SEQ ID NO:20 | X | | X | | | X | X | |
| COX2 | 146(b) | TTATTATACGAATGGGGGCTTCAA<br>SEQ ID NO:21 | | | X | X | X | | | |

TABLE 2

PART B
PRIMER AND NUCLEOTIDE COMBINATIONS FOR AD-ASSOCIATED MUTATIONS

| | | LONGER WILD-TYPE PRODUCT | | | | | |
| --- | --- | --- | --- | --- | --- | --- | --- |
| GENE | MUTATION | PRIMER SEQUENCE | OLIGO# | SENSE | LENGTH | TM | PRODUCTS |
| COX1 | 155 | TGGCCCCTAAGATAGAGGAGA<br>SEQ ID NO:9 | 94–136 | – | 21 | 55 | w22, m22 |
| COX1 | 193 | CTGATCCGTCCTAATCACAGCA<br>SEQ ID NO:22 | 95–165 | + | 22 | 57 | w25, m24, 23 |
| COX1 | 194 | AGGACTGGGAGAGATAGGAGAAGTA<br>SEQ ID NO:11 | 94–137 | – | 25 | 55 | w26, m27 |
| COX1 | 415 | ACCTACGCCAAAATCCATTTC<br>SEQ ID NO:12 | 94–125 | + | 21 | 55 | w22, m23 |
| COX2 | 20 | AGGGCGTGATCATGAAAGGTGATA<br>SEQ ID NO:23 | 94–119 | – | 24 | 62 | w25, m27 |
| COX2 | 68 | GACTAGGATGATGGCGGGCA<br>SEQ ID NO:14 | 94–118 | – | 20 | 60 | w21, m22 |

TABLE 2-continued

PART B
PRIMER AND NUCLEOTIDE COMBINATIONS FOR AD-ASSOCIATED MUTATIONS

| | | | | | | | |
|---|---|---|---|---|---|---|---|
| COX2 | 74 | GGGAGGGCGATGAGGA<br>SEQ ID NO:15 | 94–112 | − | 16 | 55 | w17, m18 |
| COX2 | 90 | CGCATCCTTTACATAACAGACGAG<br>SEQ ID NO:16 | 94–113 | + | 24 | 57 | w25, m26 |
| COX2 | 95(a) | GGCCAATTGATTTGATGGTA<br>SEQ ID NO:17 | 94–114 | − | 20 | 53 | w21, m25 |
| COX2 | 95(b) | GGCCAATTGATTTGATGGTAA<br>SEQ ID NO:18 | 94–155 | − | 21 | 53 | w22, m23 |
| COX2 | 110 | CACCAATGGTACTGAACCTACGAG<br>SEQ ID NO:19 | 94–124 | + | 24 | 57 | w26, m27, 25 |
| COX2 | 146 | ATTATTATACGAATGGGGGCTTCA<br>SEQ ID NO:20 | 94–156 | − | 24 | 57 | w26, m28, 25 |
| COX2 | 146(b) | TTATTATACGAATGGGGGCTTCAA<br>SEQ ID NO:21 | 94–138 | − | 24 | 58 | w25, m26 |

LONGER WILD-TYPE PRODUCT

| GENE | MUTATION | PRIMER SEQUENCE | dA | dC | dG | dT | ddA | ddC | ddG | ddT |
|---|---|---|---|---|---|---|---|---|---|---|
| COX1 | 155 | TGGCCCCTAAGATAGAGGAGA<br>SEQ ID NO:9 | | | | X | X | X | | |
| COX1 | 193 | CTGATCCGTCCTAATCACAGCA<br>SEQ ID NO:22 | | | X | | X | X | X | |
| COX1 | 194 | AGGACTGGGAGAGATAGGAGAAGTA<br>SEQ ID NO:11 | X | | | | | | X | |
| COX1 | 415 | ACCTACGCCAAAATCCATTTC<br>SEQ ID NO:12 | | | X | | | X | X | |
| COX2 | 20 | AGGGCGTGATCATGAAAGGTGATA<br>SEQ ID NO:23 | | | X | | | X | X | |
| COX2 | 68 | GACTAGGATGATGGCGGGCA<br>SEQ ID NO:14 | X | | | | | | X | |
| COX2 | 74 | GGGAGGGCGATGAGGA<br>SEQ ID NO:15 | | | | X | X | X | | |
| COX2 | 90 | CGCATCCTTTACATAACAGACGAG<br>SEQ ID NO:16 | X | | | | | X | X | X |
| COX2 | 95(a) | GGCCAATTGATTTGATGGTA<br>SEQ ID NO:17 | | | | X | | X | | |
| COX2 | 95(b) | GGCCAATTGATTTGATGGTAA<br>SEQ ID NO:18 | | | | X | | | X | |
| COX2 | 110 | CACCAATGGTACTGAACCTACGAG<br>SEQ ID NO:19 | | | | X | X | X | X | |
| COX2 | 146 | ATTATTATACGAATGGGGGCTTCA<br>SEQ ID NO:20 | X | X | | | | | X | X |
| COX2 | 146(b) | TTATTATACGAATGGGGGCTTCAA<br>SEQ ID NO:21 | X | | | | | | X | X |

TABLE 3

PCR PRIMERS FOR CLONAL SEQUENCE ANALYSIS

| GENE | SEQUENCE (5'→3') | | SENSE | LENGTH | PCR LENGTH | PCR RUN TEMP. | CODON ANALYSIS |
|---|---|---|---|---|---|---|---|
| COX1 | GTCCAATGCTTCACTCAGCCA | SEQ ID NO:24 | + | 21 | 333 | 60° C. | 155, 193, 194 |
| COX1 | TATGCGGGGAAACGCCAT | SEQ ID NO:25 | − | 18 | | 60° C. | |
| COX1 | GGCAACTGACTAGTTCCCCTA | SEQ ID NO:26 | + | 21 | 308 | 60° C. | 415 |
| COX1 | GTTTGGTATTGGGTTATGGCA | SEQ ID NO:27 | − | 21 | | 60° C. | |
| COX1 | GGCCATCAATTTCATCACAA | SEQ ID NO:28 | + | 20 | 341 | 60° C. | |
| COX1 | ATACCTATGTATCCAATTGGTTCT | SEQ ID NO:29 | − | 24 | | 60° C. | |
| COX1 | GGAATAATCTCCCATATTGTAACT | SEQ ID NO:30 | + | 24 | 306 | 60° C. | |
| COX1 | CAGGCCACCTACGGTGAA | SEQ ID NO:31 | − | 18 | | 60° C. | |
| COX1 | AGTGCTCTGAGCCCTAGGAT | SEQ ID NO:32 | + | 20 | 307 | 60° C. | |
| COX1 | ATTCCGGATAGGCCGAGA | SEQ ID NO:33 | − | 18 | | 60° C. | |
| COX1 | TCGGCGTAAATCTAAGTTTCTT | SEQ ID NO:34 | + | 22 | 311 | 60° C. | |
| COX1 | GGGGTTCGATTCCTTCCTT | SEQ ID NO:35 | − | 19 | | 60° C. | |
| COX2 | TCGTCAAAGTTAAATTATAGGCTA | SEQ ID NO:36 | + | 24 | 310 | 60° C. | |
| COX2 | ACCTCGTCTGTTATGTAAAGGAT | SEQ ID NO:37 | − | 19 | | 60° C. | |
| COX2 | CGCCATCATCCTAGTCCTCA | SEQ ID NO:38 | + | 20 | 280 | 60° C. | 22, 68, 74 |
| COX2 | ATGAGTGCAAGACGTCTTGTGAT | SEQ ID NO:39 | − | 23 | | 60° C. | |
| COX2 | AATCGAGTAGTACTCCCGATTGA | SEQ ID NO:40 | + | 23 | 307 | 60° C. | 90, 95, 110 |
| COX2 | GTTAGCTTTACAGTGGGCTCTAGA | SEQ ID NO:41 | − | 24 | | 60° C. | 146 |

TABLE 4

MUTATIONS IN DNA ISOLATED BY THE BOILED AND SSP DNA ISOLATION PROCEDURES (CLONAL SEQUENCING ANALYSIS)

| SAMPLE | DNA PREP | COX1:155 Val/Ile | COX1:194 Leu/Phe | COX1:415 Thr/Ala | COX2:22 Thr/Ile | COX2:95 Leu/Phe | COX2:146a Ile/Val |
|---|---|---|---|---|---|---|---|
| RI | Boiled | 50 | 40 | 50 | 30 | 20 | 20 |
| RI | SPP | 10 | | | | | |
| WO | Boiled | 10 | | 20 | 20 | | |
| WO | SPP | | | | | | |
| LF | Boiled | 20 | | 10 | 10 | 10 | 10 |
| LF | SPP | | | | | | |
| OB | Boiled | 20 | | | 20 | | |
| OB | SPP | | | | | | |
| PI | Boiled | 30 | 10 | 10 | 10 | | |
| PI | SPP | | | | | | |
| GU | Boiled | | | 10 | | | |
| GU | SPP | | | | | | |

The numerical values correspond to % heteroplasmy at each mutation locus

TABLE 5

MUTATIONAL ANALYSIS: tRNA LYSINE AND ATP SYNTHASE SUBUNIT 8

| | | | | tRNA$^{Lys}$ | | | | | ATP Synthase Subunit 8 | | | | | |
|---|---|---|---|---|---|---|---|---|---|---|---|---|---|---|
| NUCLEOTIDE # | | | | 8336 | 8345 | 8348 | 8349 | 8351 | 8371 | 8374 | 8383 | 8386 | 8392 | 8395 | 8396 |
| WILDTYPE AMINO ACID | | | | N/A | N/A | N/A | N/A | N/A | Pro | Gln | Thr | Thr | Trp | Pro | Thr |
| MUTANT AMINO ACID | | | | N/A | N/A | N/A | N/A | N/A | Pro | Gln | Thr | Thr | Trp | Pro | Ala |
| WILDTYPE NUCLEOTIDE | | | | T | C | A | C | C | C | A | T | C | G | C | A |
| MUTANT NUCLEOTIDE | | | | C | T | C | T | T | A | G | C | T | A | T | G |
| PATIENT | AG # | DIAGNOSIS | DNA ISOL. | | | | | | % HETEROPLASMY | | | | | | |
| EO | 289 | NIDDM | Boiling | 33 | 33 | 33 | 33 | 33 | 33 | 33 | 33 | 33 | 33 | 33 | 33 |
| ER | 300 | NIDDM | Boiling | 20 | 20 | 20 | 20 | 20 | 20 | 20 | 20 | 20 | 20 | 20 | 20 |
| EO | 289 | NIDDM | ProtK/SDS | 2.1 | 2.1 | 2.1 | 2.1 | 2.1 | 2.1 | 2.1 | 2.1 | 2.1 | 2.1 | 2.1 | 2.1 |
| ER | 300 | NIDDM | ProtK/SDS | 2.7 | 2.7 | 2.7 | 2.7 | 2.7 | 2.7 | 2.7 | 2.7 | 2.7 | 2.7 | 2.7 | 2.7 |

| | | | | ATP Synthase Subunit 8 | | | | | | | | | | |
|---|---|---|---|---|---|---|---|---|---|---|---|---|---|---|
| NUCLEOTIDE # | | | | 8398 | 8401 | 8404 | 8410 | 8419 | 8422 | 8423 | 8428 | 8450 | 8459 | 8463 | 8467 |
| WILDTYPE AMINO ACID | | | | Thr | Met | Ile | Pro | Leu | Thr | Leu | Phe | Leu | Asn | Tyr | His |
| MUTANT AMINO ACID | | | | Thr | Ile | Ile | Pro | Leu | Thr | Leu | Phe | Leu | Asp | Cys | His |
| WILDTYPE NUCLEOTIDE | | | | C | A | T | C | T | A | C | C | T | A | A | C |
| MUTANT NUCLEOTIDE | | | | T | C | C | A | C | G | T | T | C | G | G | T |
| PATIENT | AG # | DIAGNOSIS | DNA ISOL. | | | | | | % HETEROPLASMY | | | | | | |
| EO | 289 | NIDDM | Boiling | 33 | 33 | 33 | 33 | 33 | 33 | 33 | 33 | 33 | 33 | 33 | 33 |
| ER | 300 | NIDDM | Boiling | 20 | 20 | 20 | 20 | 20 | 20 | 20 | 20 | 20 | 20 | 20 | 20 |
| EO | 289 | NIDDM | ProtK/SDS | 2.1 | 2.1 | 2.1 | 2.1 | 2.1 | 2.1 | 2.1 | 2.1 | 2.1 | 2.1 | 2.1 | 2.1 |
| ER | 300 | NIDDM | ProtK/SDS | 2.7 | 2.7 | 2.7 | 2.7 | 2.7 | 2.7 | 2.7 | 2.7 | 2.7 | 2.7 | 2.7 | 2.7 |

| | | | | ATP Synthase Subunit 8 | | | | | | | | | | |
|---|---|---|---|---|---|---|---|---|---|---|---|---|---|---|
| NUCLEOTIDE # | | | | 8470 | 8473 | 8474 | 8485 | 8486 | 8487 | 8488 | 8491 | 8503 | 8506 | 8508 | 8509 | 8512 |
| WILDTYPE AMINO ACID | | | | Leu | Pro | Pro | Lys | Pro | Pro | Pro | Met | Asn | Tyr | Asn | Asn | Lys |
| MUTANT AMINO ACID | | | | Leu | Pro | Thr | Lys | Ser | Leu | Pro | Ile | Asn | Tyr | Ser | Asn | Lys |
| WILDTYPE NUCLEOTIDE | | | | A | T | C | G | C | C | C | A | T | T | A | C | A |
| MUTANT NUCLEOTIDE | | | | G | C | A | A | T | T | T | T | C | C | G | T | G |
| PATIENT | AG # | DIAGNOSIS | DNA ISOL. | | | | | | % HETEROPLASMY | | | | | | |
| EO | 289 | NIDDM | Boiling | 33 | 33 | 33 | 33 | 33 | 33 | 33 | 33 | 33 | 33 | 33 | 33 | 33 |
| ER | 300 | NIDDM | Boiling | 20 | 20 | 20 | 20 | 20 | 20 | 20 | 20 | 20 | 20 | 20 | 20 | 20 |

TABLE 5-continued

MUTATIONAL ANALYSIS: tRNA LYSINE AND ATP SYNTHASE SUBUNIT 8

| EO | 289 | NIDDM | ProtK/SDS | 2.1 | 2.1 | 2.1 | 2.1 | 2.1 | 2.1 | 2.1 | 2.1 | 2.1 | 2.1 | 2.1 | 2.1 | 2.1 |
| ER | 300 | NIDDM | ProtK/SDS | 2.7 | 2.7 | 2.7 | 2.7 | 2.7 | 2.7 | 2.7 | 2.7 | 2.7 | 2.7 | 2.7 | 2.7 | 2.7 |

 Silent Mutation

 Missence Mutation

 tRNA Mutation

A very similar pattern emerges from primer extension analysis of 11 blood samples isolated by the boiling and the SPP procedures (Table 6). In the boiled DNA preparations, mutant alleles with allelic frequencies ranging from 10–34% are detected for all the samples at the five interrogated codon sites in the COX1 and COX2 genes. Analysis of the proteinase K treated preparations revealed that the DNA from these samples is predominantly wild type and mutant alleles are present at <5% frequency.

Table 7 summarizes the results of a primer extension study of 8 samples whose DNA is isolated by the boiling procedure and PSPC sample preparation method. Besides including additional AD-associated codons, nucleotide 3460 in the ND1 gene associated with Leber Optic Heriditary Neuropathy (LHON) and nucleotide 3243 in the tRNA$^{Leu}_{(UUR)}$ gene associated with the MELAS (Mitochondrial Myopathy, Encephalopathy, Lactic Acidosis, and Stroke-like Episodes) syndrome are also monitored. The analysis reveals that the boiling procedure selectively increased the relative proportion of mutant alleles at codons 155, 194 and 415 of the COX1 gene and codons 22, 95 and 146 in the COX2 gene. In contrast, the relative abundance of the other AD-associated mutant alleles is not altered by the boiling procedure. Further, no increase in mutant allelic frequencies at the LHON and MELAS loci is seen in using the boiling procedure.

TABLE 6

MUTATIONS IN DNA ISOLATED BY THE BOILED AND SSP DNA ISOLATION PROCEDURES (PRIMER EXTENSION ANALYSIS)

| SAMPLE | DNA PREP | COX1:194 Leu/Phe | COX1:415 Thr/Ala | COX2:22 Thr/Ile | COX2:95 Leu/Phe | COX2:146a Ile/Val |
|---|---|---|---|---|---|---|
| RI | Boiled | 30.7 | 34 | 27 | 21.6 | 20.4 |
| RI | SPP | 4.9 | 3.9 |  | 3.2 | 3.4 |
| WO | Boiled | 11.4 | 2.5 | 14.1 | 8.9 | 8.6 |
| WO | SPP |  |  | 1.8 | 3.7 | 2.9 |
| GM | Boiled | 20.8 | 16.9 | 24.3 | 19.4 | 20.0 |
| GM | SPP |  |  |  |  |  |
| SH | Boiled | 17.0 | 19.7 | 22.9 | 17.2 | 20.6 |
| SH | SPP |  |  |  |  |  |
| GA | Boiled | 16.5 | 12.5 | 19.3 | 15.0 | 16.0 |
| GA | SPP |  |  |  |  |  |
| KA | Boiled | 16.3 | 13.1 | 25.0 | 20.1 | 21.6 |
| KA | SPP | 4.4 |  |  |  |  |
| PI | Boiled | 16.4 | 20.2 | 26.2 | 22.4 | 23.6 |
| PI | SPP |  |  |  |  |  |
| LF | Boiled | 8.6 | 8.0 | 14.9 | 18.9 | 9.4 |
| LF | SPP | 6.1 |  |  |  |  |
| OB | Boiled | 13.9 | 12.7 | 21.2 | 22.7 | 18.2 |
| OB | SPP | 3.5 |  |  | 2.9 |  |
| GU | Boiled | 13.5 | 15.2 | 20.3 | 19.0 | 16.4 |
| GU | SPP |  |  |  |  |  |
| RD | Boiled | 14.0 | 13.8 | 17.3 | 12.6 | 13.7 |
| RD | SPP |  |  |  |  |  |

The numerical values correspond to % heteroplasmy at each mutation locus

TABLE 7

PART A
THE BOILED DNA ISOLATION PROCEDURE SELECTIVELY INCREASES MUTATIONAL FREQUENCY AT SPECIFIC CONDONS

| SAMPLE | DNA PREP | COX1:155 | COZ1:193 Val/Ala | COX1:193 Val/Ile | COX1:194 Leu/Phe | COX1:415 Thr/Ala | COX2:22 Thr/Ile | COX2:68 Leu/Phe | COX2:74 Val/Ala |
|---|---|---|---|---|---|---|---|---|---|
| ADRC #2468 | Boiled | 10.1 |  |  | 7.6 | 9.0 | 17.2 |  |  |
| ADRC #2468 | PSPC |  |  |  |  |  |  |  |  |
| ADRC #2583 | Boiled | 8.3 |  |  | 8.7 | 12.8 | 15.7 |  |  |
| ADRC #2583 | PSPC |  |  |  |  |  |  |  |  |

TABLE 7-continued

PART A
THE BOILED DNA ISOLATION PROCEDURE SELECTIVELY INCREASES MUTATIONAL FREQUENCY AT SPECIFIC CONDONS

| SAMPLE | DNA PREP | COX1:155 | COZ1:193 Val/Ala | COX1:193 Val/Ile | COX1:194 Leu/Phe | COX1:415 Thr/Ala | COX2:22 Thr/Ile | COX2:68 Leu/Phe | COX2:74 Val/Ala |
|---|---|---|---|---|---|---|---|---|---|
| ADRC #2473 | Boiled | 12.6 | | | 22.9 | 25.7 | 21.3 | | |
| ADRC #2473 | PSPC | | | | | | | | |
| ADRC #2489 | Boiled | 11.2 | | | 21.3 | 17.0 | 16.6 | | |
| ADRC #2489 | PSPC | | | | 1.5 | | | | |
| ADRC #2485 | Boiled | 12.3 | | | 19.5 | 20.7 | 20.5 | | |
| ADRC #2485 | PSPC | | | | | | | | |
| ADRC #2362 | Boiled | 13 | | | 20.3 | 24.9 | 26.1 | | |
| ADRC #2362 | PSPC | | | | 3.7 | | | | |
| ADRC #2581 | Boiled | | | | 13.8 | 9.1 | 7.7 | | |
| ADRC #2581 | PSPC | | | | | | | | |
| ADRC #2486 | Boiled | 14.1 | | 3.4 | 22.8 | 27.5 | 31.3 | | |
| ADRC #2486 | PSPC | | | | | | | | |

The numerical values correspond to % heteroplasmy at each mutation locus

TABLE 7

PART B
THE BOILED DNA ISOLATION PROCEDURE SELECTIVELY INCREASES MUTATIONAL FREQUENCY AT SPECIFIC CONDONS

| SAMPLE | DNA PREP | COX2:90 Val/Ile | COX2:95 Leu/Pro | COX2:95 Leu/Phe | COX2:110 Tyr/Cys | COX2:110 Tyr/His | COX2:146a Ile/Val | ND1-3460 (LHON) | tRNA(Leu-3243(MELAS) |
|---|---|---|---|---|---|---|---|---|---|
| ADRC #2468 | Boiled | | | 23.7 | | | 20.3 | 2.0 | |
| ADRC #2468 | PSPC | | | 3.6 | | | 1.8 | 2.3 | |
| ADRC #2583 | Boiled | | | 25.2 | | | 21.9 | 3.3 | |
| ADRC #2583 | PSPC | | | 2.4 | | | 5.2 | 1.5 | |
| ADRC #2473 | Boiled | | | 25.4 | | | 24.2 | 1.3 | |
| ADRC #2473 | PSPC | | | 3.2 | | | 5.4 | 1.7 | |
| ADRC #2489 | Boiled | | | 21.6 | | | 19.4 | 1.7 | |
| ADRC #2489 | PSPC | | | 3.7 | | | 4.9 | 1.8 | |
| ADRC #2485 | Boiled | | | 24.9 | | | 24.2 | 1.4 | 2.7 |
| ADRC #2485 | PSPC | | | 3.5 | | | | 1.9 | |
| ADRC #2362 | Boiled | 4.0 | | 27.6 | | | 27.9 | 2.1 | |
| ADRC #2362 | PSPC | | | 3.6 | | | 4.2 | 2.1 | 2.5 |
| ADRC #2581 | Boiled | | | 10.1 | | | 11.3 | 1.4 | 0.3 |
| ADRC #2581 | PSPC | | | | | | 4.4 | 1.7 | |
| ADRC #2486 | Boiled | | | 38.8 | | | 36.6 | 2.4 | 3.2 |
| ADRC #2486 | PSPC | | | 5.0 | | | 3.9 | 1.9 | 0.3 |

The numerical values correspond to % heteroplasmy at each mutation locus

Increased Mutation Frequency at the Six Loci Does Not Arise Due to Artifacts Introduced in the Extraction Procedure or in the PCR Step Since the boiling procedure provides a crude DNA preparation, it is conceivable that a cellular contaminant may compromise the fidelity of the AmpliTaq DNA polymerase in the PCR reaction used for preparing the primer extension reaction templates. As seen in Table 8, nearly identical mutant allelic frequencies are obtained upon substitution of AmpliTaq DNA polymerase with UlTma™ DNA polymerase, a high fidelity enzyme with 3'–5' proofreading activity.

Figure 4:
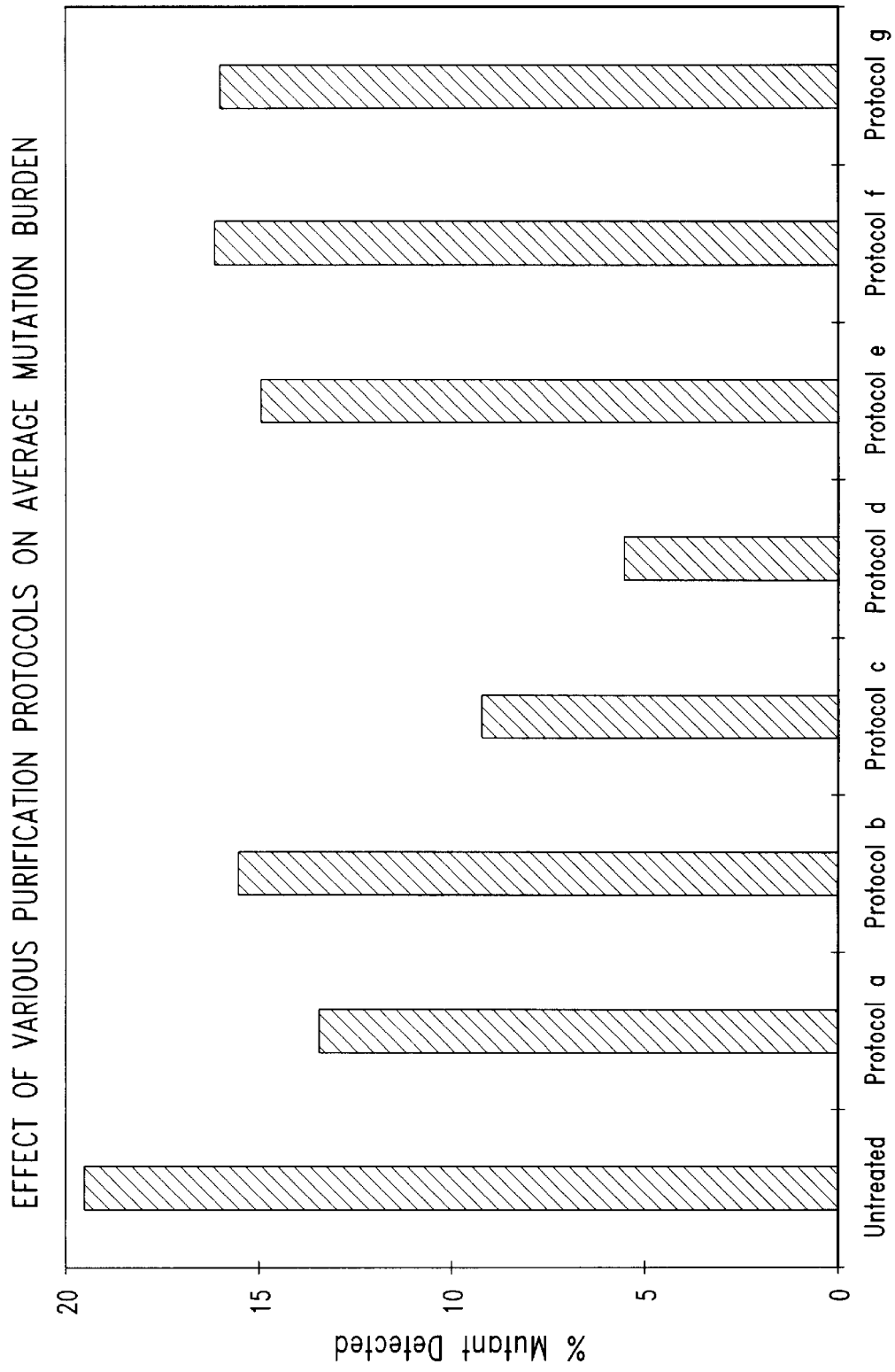
FIG. 4 illustrates the effect of various purification protocols on average mutational burden.
Figure 6A:
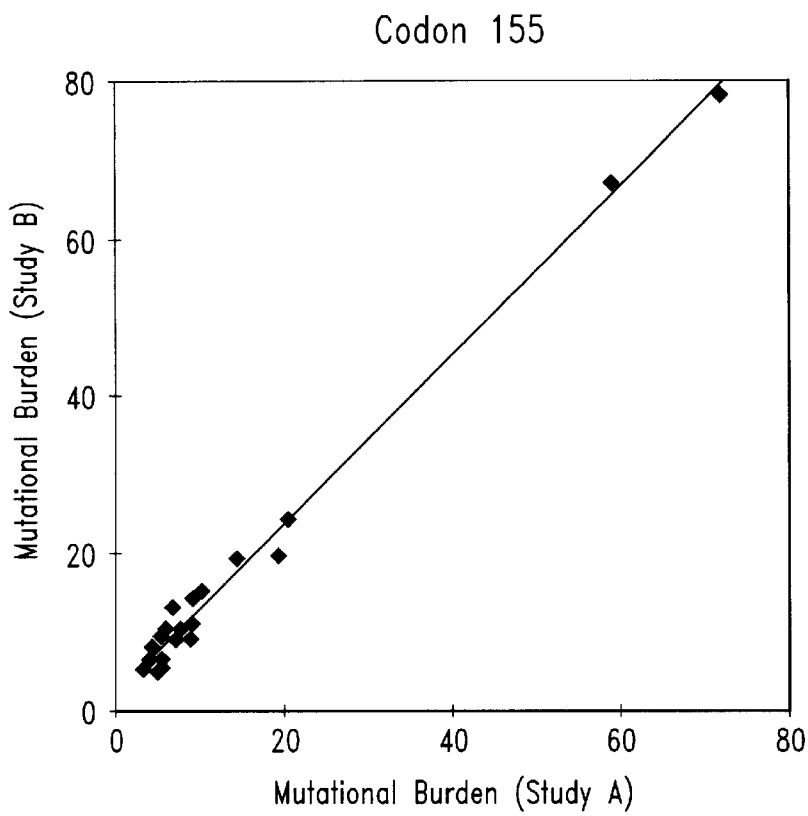
FIGS. 6A–6G represents mutational burdens observed for two studies for several individual codons of the COXI and COXII genes, as well as the sum of these codons (total mutational burden).
Figure 6B:
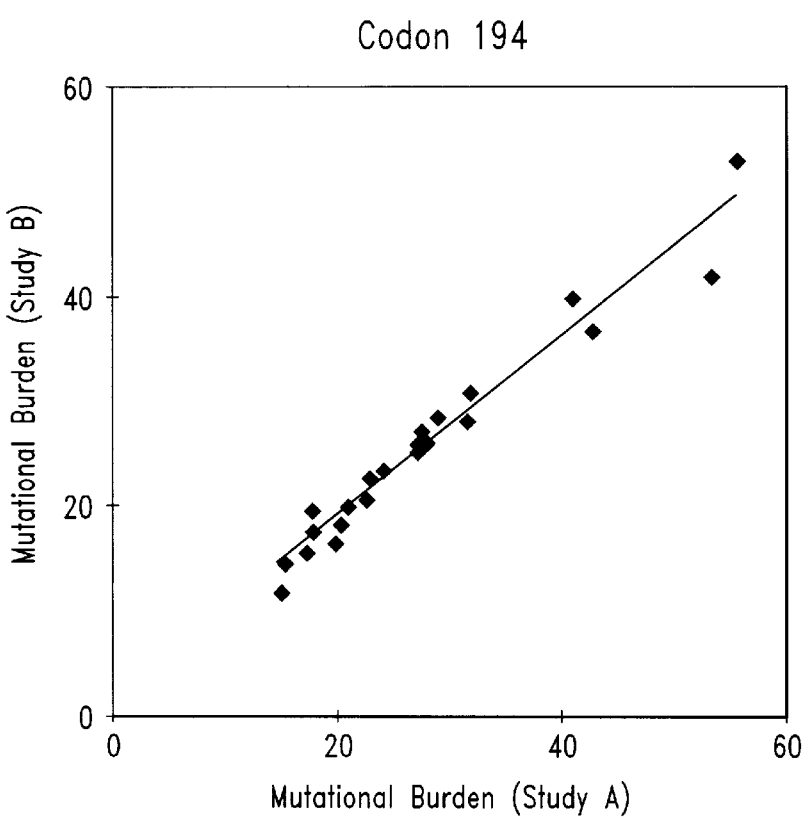
Figure 6C:
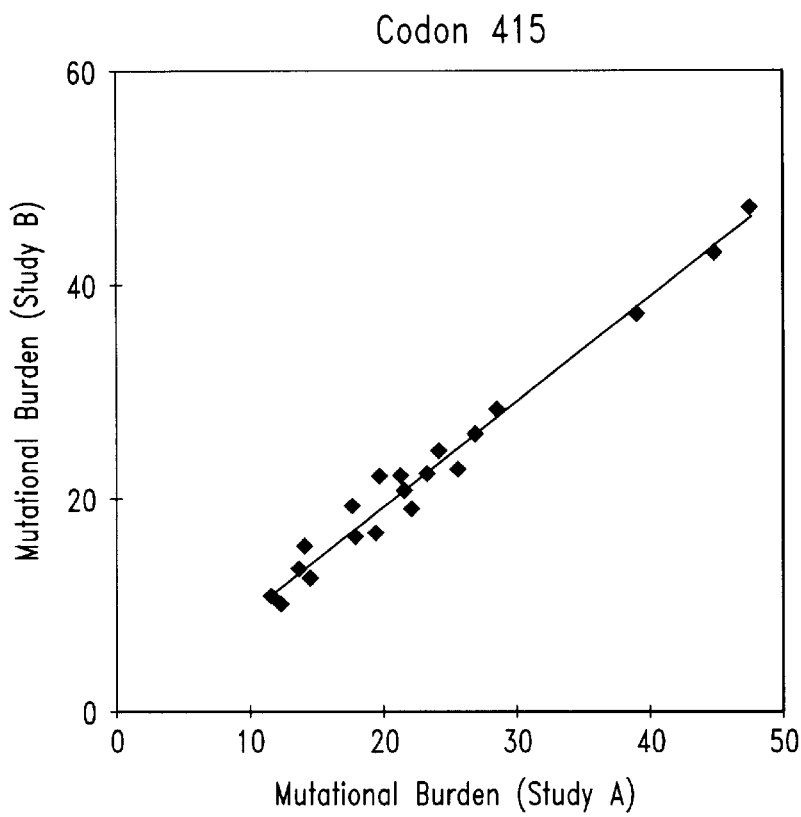
Figure 6D:
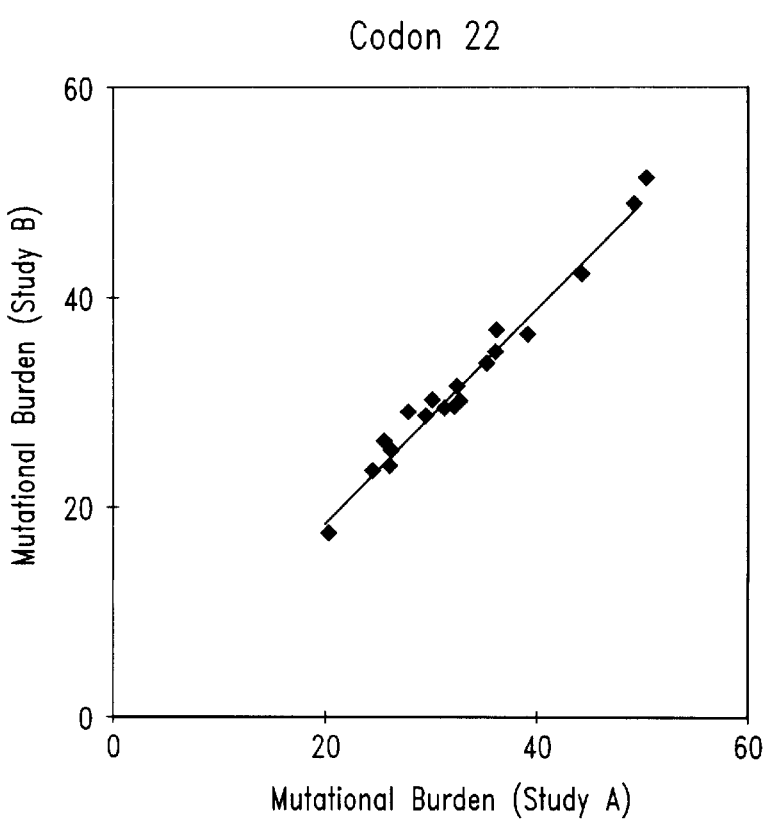
Figure 6E:
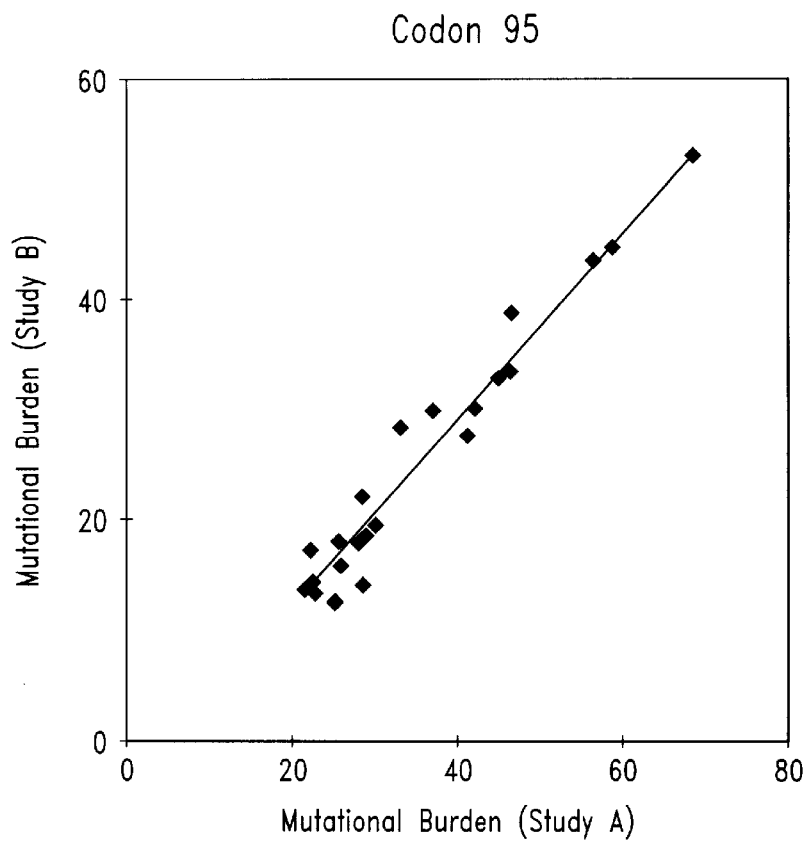
Figure 6F:
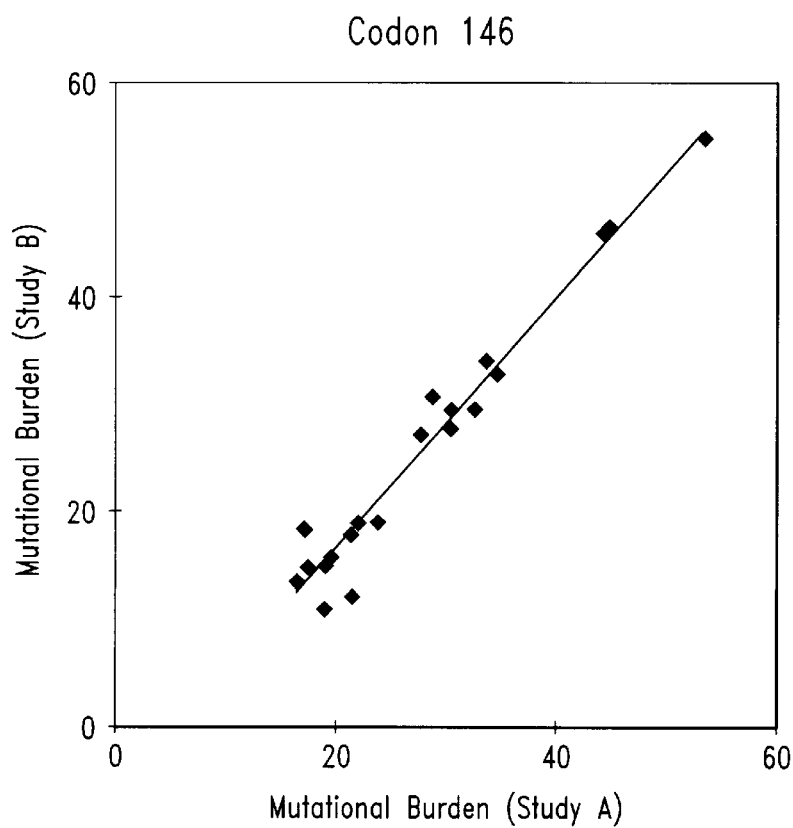
Figure 6G:
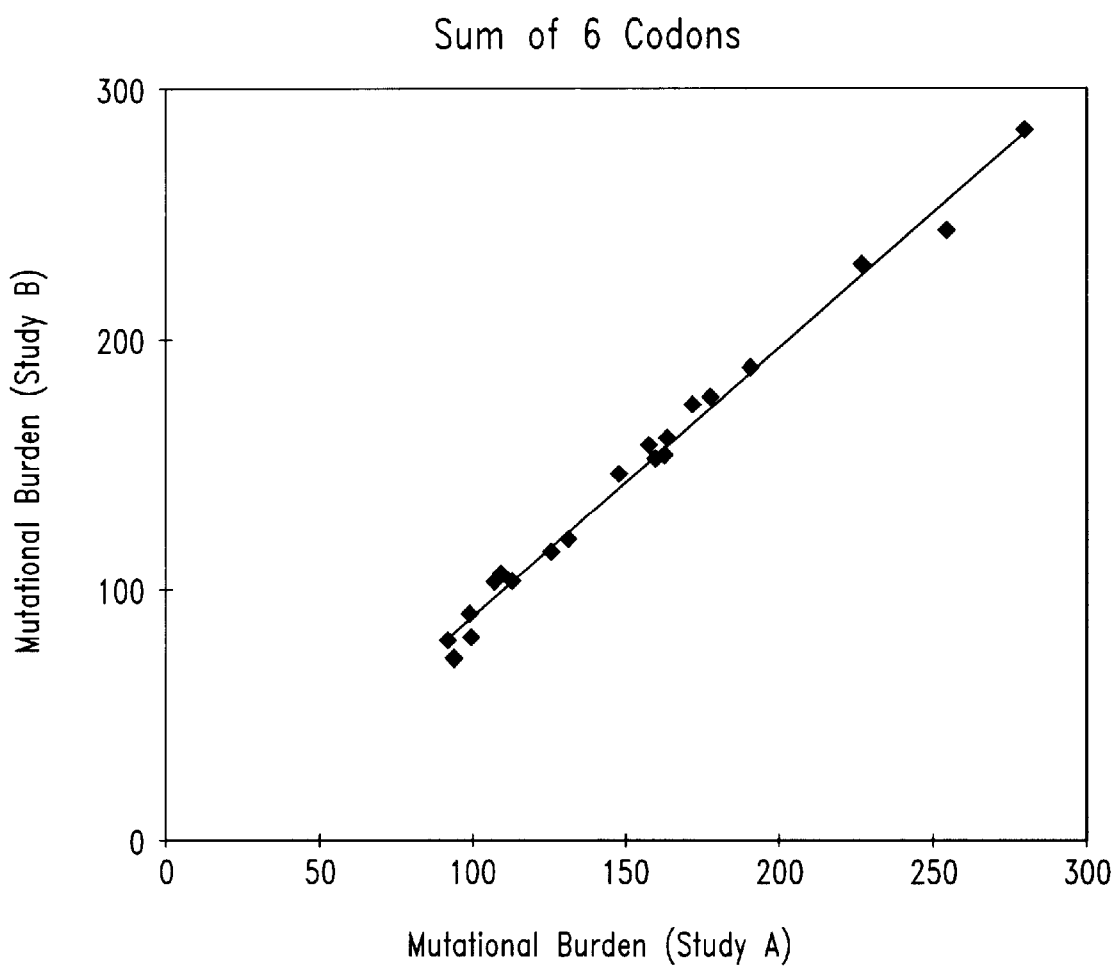

A crude DNA preparation obtained by the boiling procedure on a buffy coat extract is further subjected to several purification protocols. These conditions are chosen to ascertain if the mutations at the selected codon sites in mitochondrial DNA are indeed due to base changes, and not arising from base modification such as malondialdehyde adduct formation. The protocols are as follows: (a) ethanol precipitation, (b) phenol/chloroform extraction, (c) proteinase K digestion followed by organic extraction, (d) proteinase K digestion followed by heat denaturation of proteases and isolation of DNA by ultrafiltration, (e) base treatment followed by organic extraction, (f) acid treatment followed by organic extraction, (g) guanidinium isothiocyanate treatment followed by ultrafiltration isolation of DNA. The purified DNA fractions and an untreated fraction are PCR-amplified and the results of primer extension analysis (Table 9) indicate that the proteinase K treatment significantly affects detection of AD-associated mutant alleles. This is graphically depicted in FIG. 4, which plots average mutational burden (average of mutant allele frequencies at codon sites COX1:155, COX1:194, COX1:415, COXII:22, COXII:95 and COXII:146) obtained with each purification protocol.

TABLE 8

USE OF DIFFERENT DNA POLYMERASE IN PCR OF DNA ISOLATED BY THE BOILED PROCEDURE

| SAMPLE | PCR ENZYME | COX1:194 Leu/Phe | COX1:415 Thr/Ala | COX2:22 Thr/Ile | COX2:95 Leu/Phe | COX2:146A Ile/Val |
|---|---|---|---|---|---|---|
| GA | Taq | 16.5 | 12.5 | 19.3 | 15.0 | 16.0 |
| GA | UITma | 17.6 | 11.7 | 13.4 | 15.2 | 13.7 |

The numerical values correspond to % heteroplasmy at each mutation locus

TABLE 9

EFFECT OF VARIOUS PURIFICATION PROTOCOLS ON BOILED DNA PREPARATION

| PROCEDURE | COX1:155 Val/Ile | COX1:194 Leu/Phe | COX1:415 Thr/Ala | COX2:22 Thr/Ile | COX2:95 Leu/Phe | COX2:146A Ile/Val |
|---|---|---|---|---|---|---|
| Untreated | 15.1 | 22.0 | 7.2 | 28.0 | 20.9 | 24.0 |
| a | 12.7 | 16.5 | 5.2 | 11.0 | 16.3 | 18.9 |
| b | 12.2 | 18.1 | 6.1 | 14.1 | 21.0 | 21.6 |
| c | 4.9 | 12.5 | 3.8 | 7.6 | 12.7 | 13.6 |
| d | 5.2 | 4.7 | | 4.0 | 9.1 | 10.3 |
| e | 12.6 | 17.6 | N/A | 14.1 | 21.5 | 24.0 |
| f | 13.3 | 15.8 | 6.2 | 16.5 | 21.7 | 23.7 |
| g | 14.7 | 16.8 | 7.3 | 14.9 | 20.8 | 21.8 | a Ethanol/precipitation
b phenol/chloroform extraction
c Proteinase K/phenol/chloroform
d Proteinase K/ultrafiltration
e NaOH/phenol/chloroform
f pH 5/phenol/chloroform
g Guanidinium isothiocyanate/ultrafiltration Next, various PCR cycles and initial target concentrations for the initial PCR step of the primer extension assay are investigated to evaluate these parameters in reproducing the heteroplasmy present in the input target. A number of 20% mutant/wildtype plasmid mixtures are utilized at various starting concentrations in PCR reactions, and are amplified using different PCR cycles. It should be noted that the ~1 µg amount of cellular DNA typically used as input target contains ~1 fmol of mtDNA, and therefore is in the range of target amounts investigated in this experiment. A DNA sample prepared by the boiling procedure from blood sample ADRC-2588 is also included in the PCR cycle study. Table 10 (A, B) shows that the mutant/wild type ratios reported by the assay using various input target concentrations and PCR cycles are in excellent agreement with the levels of heteroplasmy in the input DNA samples. Further, increasing the PCR cycles does not alter the mutant allele frequencies for ADRC-2588.

TABLE 10 A

INFLUENCE of INITIAL PCR TARGET CONCENTRATION on HETEROPLASMY at AD-LINKED CODONS

| INITIAL PCR TARGET CONC. (fmol) | COX1:194 Leu/Phe | COX1:415 Thr/Ala | COX2:22 Thr/Ile | COX2:95 Leu/Phe | COX2:146a Ile/Val |
|---|---|---|---|---|---|
| 0.1 | 25.4 | | 24.7 | | 24.7 |
| 1 | 24 | | 25.8 | | 24.5 |
| 10 | 27.3 | | 22.5 | | 23.2 |

Mutational analysis of PCR products obtained from amplification of 20% mutant/plasmid co-mixes at different initial PCR target concentrations.

TABLE 10 B

INFLUENCE of PCR CYCLES on PRIMER EXTENSION ANALYSIS

| SAMPLE | PCR CYCLES | COX1:194 Leu/Phe | COX2:22 Thr/Ile | COX2:95 Leu/Phe |
|---|---|---|---|---|
| PLASMID (20%) | 15 | 17.6 | 21.4 | |
| PLASMID (20%) | 20 | 24.3 | 24.1 | |
| PLASMID (20%) | 25 | 27.1 | 19.5 | |
| PLASMID (20%) | 30 | 26.9 | 21.9 | |
| ADRC-2588 | 20 | 14.8 | 17.7 | 9.7 |
| ADRC-2588 | 25 | 22.3 | 23.3 | 14.5 |
| ADRC-2588 | 30 | 24 | 23.7 | 12.6 |

TABLE 10 C

EFFECT of THE BOILING PROCEDURE on HETEROPLASMY at AD-ASSOCIATED CODONS

| SAMPLE | COX-1:194 Leu/Phe | COX-1:415 Thr/Ala | COX-2:22 Thr/Ile | COX-2:95 Leu/Phe | COX-2:146a Ile/Val |
|---|---|---|---|---|---|
| ADRC-2588 + COX1 plasmid | | | 16.9 | 6.6 | 8.7 |
| ADRC-2588 + COX2 plasmid | 13.6 | 10.7 | | | |
| COX1 plasmid COX2 plasmid | | | | | |
| ADRC-2588 | 18.4 | 14.2 | 23.1 | 10 | 9.9 |

Plasmids containing either the COX1 or COX2 inserts were subjected to the boiled procedure in the presence (1,2) or absence of buffy coat (3,4) prepared from ADRC-2588 blood. A separate buffy coat fraction (5) was boiled and used as a positive control.

The following experiment is carried out to rule out the possibility that the boiling procedure chemically modified the DNA, or that a cellular component is mutagenic in the boiling step. Buffy coat preparation from a blood sample (ADRC-2588) are spiked with wild type plasmids containing COXI and COXII gene inserts, respectively, and the DNA is extracted by the boiling procedure. A 100 fold molar excess of plasmid is used in the experiment, based on the estimate of mtDNA in the buffy coat fraction. The COXI, COXII and buffy coat fraction are also boiled separately. The resulting DNA mixtures are PCR amplified and analyzed for the presence of mutant alleles at the codon sites which had earlier been shown to be affected by the boiling procedure (Table 6, 7). As seen in Table 10C, mutant alleles are not detected in plasmids subjected to the boiling procedure (entry 3,4). As anticipated, the DNA isolated from the buffy coat is heteroplasmic (entry 5), with nearly identical mutant allele frequencies as reported in Table 7. Mutant alleles are only observed in the COXII gene when COXI and buffy coat fraction are subjected to the boiling procedure, and the converse is true for the COXII/buffy coat mixture (entry 1,2). This provides convincing evidence that cellular components in the buffy coat are not mutagenic, and that the boiling procedure does not induce mutations in the plasmids.

Mutant Allele Frequencies in DNA Isolated from Buffy Coat Fractions Prepared by the Accuspin and Dextran Procedure Buffy coat fractions are prepared from 36 whole blood samples by the Accuspin and Dextran procedures, described below in the Examples. DNA is isolated by the boiling procedure and then analyzed by the primer extension assay. The total mutational burden (sum of mutant allele frequencies at codon sites COX1:155, COX1:194, COX1:415, COXII:22, COXII:95 and COXII:146) obtained for the two procedures is plotted in FIG. 5. In general, the mutational burden is approximately 50% lower in DNA from Accuspin buffy coat and there is a good correlation between the two procedures. The differences in total mutational burden suggests variation in cellular populations in the two buffy coat fractions.

Reproducibility of the Overall Primer Extension Assay

A duplicate set of Accuspin buffy coat fractions of 22 blood samples is prepared, following which the DNA is extracted by the boiling procedure and analyzed by the primer extension assay. FIG. 6 presents a graphical representation of mutant allele frequency for individual codons and total mutational burden. Inherent in the analysis is the variability of DNA sample preparation, PCR amplification and the primer extension reaction. The close correlation observed between the two independent studies (FIG. 6) highlights the excellent reproducibility of the overall primer extension-based mutational assay.

AD Patients Show Elevated Mutational Burden at Specific Loci in mtDNA-encoded COX1 and COXII Genes As discussed above, the boiling procedure selectively increases the relative proportion of mutant to normal alleles at six nucleotide positions in the COX1 and COXII genes, and does not alter the relative abundance of mutant alleles at other AD-linked nucleotide loci.

Sequencing and primer extension studies have revealed these six mutations at nucleotide positions 6366, 6483 and 7146 in COXI codons 155, 194 and 415 and nucleotide positions 7650, 7868 and 8021 in COXII codons 22, 95 and 146 appear to be linked. In general, when one of these mutations appears, the other five mutations also appear. However, rare exceptions do occur, particularly when the mutation at codon 415 appears as a homoplasmic allele.

In the process of improving the sensitivity of our detection assay, we have discovered that most controls (demented, diseased and cognitively normal) also exhibit low levels of these six mutations. However, by using our multiplexed primer extension assay, we have been able to demonstrate quantitative differences in the abundance of mutant alleles at each of these bases between some Alzheimer's disease patients and controls.

A blinded mutational analysis is carried out on DNA extracted by the boiling procedure on Accuspin buffy coat fractions. Seventy-three controls and 65 patients with a clinical diagnosis of possible/probable AD (sproadic, late onset form) are examined. The controls comprise 43 cognitively normal aged matched individuals, 10 patients with non-insulin dependent diabetes mellitus (NIDDM), 16 individuals with Parkinson's disease and 2 Pick's disease patients. (Table 11). The percentage of mutant to normal DNA is determined at each of six AD-associated nucleotide positions in mtDNA. AD patients as a group have significantly higher mutant allele frequencies as compared to the control group (FIG. 1).

The mutant allele frequences are then used to calculate Fisher scores using the Fisher multivariate discriminant analysis technique. The Fisher score is reflective of the overall mutational burden of the individual and a plot of cumulative percent of cases versus Fisher score highlights the difference in mutational burden between the AD and the control groups (FIG. 2).

The AD patients as a group are characterized by high Fisher scores while controls are distinguished by low Fisher scores. Fisher score thresholds can therefore be applied to separate AD patients from controls and to define the sensitivity and specificity of the assay. Thus, approximately 20% of all AD cases have Fisher scores above 350 while no controls exceed this value (20% sensitivity, 100% specificity). At an intermediate Fisher score threshold of 270, approximately 55% of AD cases have Fisher scores exceeding this value, whereas only 10% of controls exceed this level of mutational load (55% sensitivity, 90% specificity).

Finally, it is rare for AD cases to have low Fisher scores while it is common for controls to have low scores. Approximately 50% of controls have Fisher scores below 170 while only 5% of AD cases have Fisher scores below this value. Low Fisher scores, therefore, represent a negative risk factor for AD.

The Fisher multivariate discriminant analysis of mutant mitochondrial allele frequencies serves two purposes. First, it is used to separate two distinct ppopulations (AD and controls) based on differences in mutational burden. Second, the technique can be used for AD diagnosis, based on rules of classification that can be used to optimally assign an individual to the two populations.

As seen above, the Fisher score threshold is an important parameter for classification. Fisher score values are dependent on the size of the dataset and also on the normalization method applied to the data. Since the sample size determines the absolute value of the Fisher score, it should be obvious to those skilled in the art that a large database is necessary for classification.

TABLE 11

PART A
Mutant Allel Frequencies at AD-Associated Loci in Cytochrome c Oxidase Subunit 1 & 2 Genes

| Patient | Diagnosis | COX1:155 | COX1:194 | COX1:415 | COX2:22 | COX2:95 | COX2:146 | Fisher Score |
|---|---|---|---|---|---|---|---|---|
| 474 | AD | 20.7 | 22.3 | 19.4 | 23.4 | 14.8 | 18.5 | 259.2 |
| 331 | AD | 11.1 | 30.8 | 21.5 | 23.4 | 22.6 | 21.3 | 244.2 |
| 378 | AD | 25.5 | 25.8 | 22.1 | 29.4 | 27.6 | 28.9 | 283.9 |
| 379 | AD | 31.3 | 36.7 | 28.4 | 36.9 | 29.9 | 30.3 | 398.9 |
| 380 | AD | 30.0 | 30.8 | 22.4 | 31.4 | 32.8 | 32.4 | 308.6 |
| 381 | AD | 12.3 | 11.8 | 10.0 | 25.1 | 13.6 | 14.1 | 282.8 |
| 383 | AD | 69.0 | 20.4 | 12.5 | 28.6 | 17.8 | 15.0 | 296.8 |
| 384 | AD | 36.3 | 25.8 | 20.8 | 34.6 | 33.4 | 29.3 | 352.4 |
| 385 | AD | 14.6 | 19.6 | 13.1 | 23.9 | 13.4 | 13.2 | 290.9 |
| 387 | AD | 19.6 | 19.3 | 15.6 | 26.1 | 19.6 | 17.8 | 285.4 |
| 388 | AD | 19.2 | 15.5 | 19.2 | 30.2 | 18.0 | 15.4 | 324.0 |
| 809 | AD | 15.7 | 17.8 | 10.3 | 21.4 | 13.0 | 9.8 | 272.2 |
| 936 | AD | 7.7 | 19.6 | 11.8 | 25.0 | 13.5 | 12.0 | 306.8 |
| 938 | AD | 20.4 | 24.4 | 10.8 | 18.0 | 16.3 | 17.2 | 223.6 |
| 964 | AD | 40.9 | 37.7 | 34.3 | 48.9 | 47.1 | 47.6 | 457.4 |
| 1017 | AD | 21.1 | 14.5 | 11.4 | 17.5 | 13.3 | 7.7 | 213.7 |
| 1041 | AD | 17.2 | 14.6 | 15.3 | 24.3 | 14.7 | 13.6 | 267.7 |
| 1044 | AD | 30.4 | 29.2 | 21.8 | 34.1 | 29.3 | 27.4 | 365.5 |
| 1053 | AD | 29.1 | 32.4 | 27.4 | 40.8 | 31.7 | 29.1 | 435.6 |
| 1054 | AD | 41.1 | 39.5 | 35.2 | 40.2 | 38.3 | 34.8 | 404.1 |
| 1055 | AD | 41.0 | 29.1 | 30.8 | 39.6 | 52.1 | 31.8 | 341.8 |
| 1056 | AD | 14.7 | 19.9 | 16.1 | 23.7 | 15.0 | 12.3 | 277.2 |
| 1091 | AD | 20.8 | 19.0 | 14.4 | 20.9 | 17.6 | 14.1 | 235.2 |
| 1092 | AD | 14.4 | 12.5 | 12.2 | 19.6 | 12.0 | 8.8 | 225.2 |
| 1043 | AD | 17.8 | 15.8 | 14.3 | 23 | 17.1 | 15 | 247.9 |
| 676 | AD | 17.9 | 10.0 | 9.4 | 20.9 | 13.1 | 12.5 | 233.2 |

TABLE 11

PART B
Mutant Allel Frequencies at AD-Associated Loci in Cytochrome c Oxidase Subunit 1 & 2 Genes

| Patient | Diagnosis | COX1:155 | COX1:194 | COX1:415 | COX2:22 | COX2:95 | COX2:146 | Fisher Score |
|---|---|---|---|---|---|---|---|---|
| 984 | AD | 18.9 | 31.8 | 21.9 | 31.8 | 18.8 | 19.9 | 382.7 |
| 985 | AD | 13.3 | 15.7 | 11.9 | 18.6 | 11.6 | 14.0 | 210.0 |
| 986 | AD | 0.1 | 0.9 | 0.0 | 14.0 | 0.0 | 0.9 | 190.6 |
| 987 | AD | 26.1 | 28.9 | 27.3 | 45.6 | 29.8 | 30.6 | 486.3 |
| 988 | AD | 32.0 | 42.7 | 34.0 | 50.4 | 37.2 | 37.4 | 544.6 |
| 992 | AD | 17.8 | 20.9 | 14.7 | 28.1 | 27.7 | 22.8 | 283.4 |
| 994 | AD | 21.9 | 18.1 | 17.9 | 19.2 | 19.1 | 16.9 | 185.4 |
| 995 | AD | 18.1 | 25.4 | 18.0 | 26.0 | 20.0 | 16.2 | 300.1 |
| 996 | AD | 45.7 | 52.6 | 50.5 | 51.4 | 57.2 | 50.9 | 456.3 |
| 998 | AD | 20.9 | 17.2 | 20.7 | 32.5 | 23.8 | 19.6 | 329.6 |
| 999 | AD | 18.0 | 21.3 | 17.2 | 25.9 | 19.8 | 15.7 | 288.8 |
| 1000 | AD | 11.9 | 11.5 | 23.7 | 19.7 | 15.7 | 13.2 | 156.0 |
| 1001 | AD | 10.2 | 8.1 | 11.2 | 15.0 | 12.8 | 10.0 | 140.5 |
| 1002 | AD | 16.3 | 20.3 | 20.4 | 26.3 | 22.7 | 16.9 | 265.5 |
| 1003 | AD | 17.2 | 23.3 | 20.6 | 24.5 | 19.7 | 17.1 | 260.6 |
| 1007 | AD | 21.9 | 25.0 | 20.5 | 30.4 | 31.1 | 25.5 | 295.4 |
| 1008 | AD | 14.8 | 12.4 | 13.6 | 21.7 | 21.1 | 16.7 | 201.1 |
| 1009 | AD | 28.1 | 28.5 | 23.9 | 33.0 | 34.8 | 27.4 | 322.8 |
| 1010 | AD | 16.2 | 15.4 | 12.8 | 19.0 | 16.9 | 12.7 | 203.9 |
| 1012 | AD | 15.8 | 21.7 | 15.8 | 21.5 | 18.0 | 14.0 | 243.3 |
| 675 | AD | 49.6 | 43.1 | 35.5 | 40.5 | 34.1 | 37.7 | 432.8 |
| 676 | AD | 17.9 | 10.0 | 9.4 | 20.9 | 13.1 | 12.5 | 283.2 |
| 677 | AD | 49.2 | 42.9 | 37.9 | 39.8 | 33.6 | 37.4 | 415.1 |
| 678 | AD | 12.0 | 10.9 | 5.2 | 12.2 | 8.5 | 8.6 | 151.6 |
| 683 | AD | 7.8 | 16.4 | 10.8 | 18.1 | 12.6 | 11.8 | 208.4 |
| 684 | AD | 6.9 | 24.8 | 9.5 | 21.5 | 11.2 | 10.6 | 296.6 |

TABLE 11

PART C

Mutant Allele Frequencies at AD-Associated Loci in Cytochrome c Oxidase Subunit 1 & 2 Genes

| Patient | Diagnosis | COX1:155 | COX1:194 | COX1:415 | COX2:22 | COX2:95 | COX2:146 | Fisher Score |
|---|---|---|---|---|---|---|---|---|
| 685 | AD | 4.1 | 10.8 | 10.4 | 31.0 | 21.4 | 20.3 | 310.5 |
| 686 | AD | 11.0 | 16.6 | 14.4 | 18.6 | 18.3 | 18.7 | 170.1 |
| 693 | AD | 24.4 | 24.7 | 16.7 | 22.3 | 16.0 | 21.0 | 256.9 |
| 694 | AD | 18.5 | 16.8 | 12.5 | 26.4 | 18.3 | 19.7 | 288.0 |
| 696 | AD | 15.4 | 13.6 | 10.0 | 16.4 | 8.8 | 12.2 | 193.4 |
| 698 | AD | 21.4 | 16.5 | 14.1 | 21.7 | 14.5 | 16.7 | 239.2 |
| 699 | AD | 29.1 | 29.5 | 21.7 | 32.7 | 27.8 | 24.9 | 358.0 |
| 700 | AD | 16.9 | 13.7 | 11.3 | 18.1 | 15.7 | 18.7 | 176.5 |
| 702 | AD | 21.9 | 27.2 | 16.5 | 24.0 | 16.5 | 19.9 | 288.5 |
| 703 | AD | 9.1 | 14.1 | 3.7 | 13.8 | 5.3 | 1.9 | 216.4 |
| 704 | AD | 8.4 | 6.9 | 5.2 | 13.3 | 3.3 | 5.8 | 171.1 |
| 705 | AD | 9.9 | 12.4 | 8.3 | 24.6 | 11.7 | 12.1 | 293.8 |
| 706 | AD | 17.0 | 11.1 | 11.5 | 31.1 | 22.7 | 18.4 | 232.3 |
| 0013 | Aged Control | 4.2 | 10.1 | 12.0 | 16.8 | 8.0 | 3.0 | 195.3 |
| 0019 | Aged Control | 12.2 | 6.9 | 6.7 | 14.8 | 9.4 | 6.7 | 169.6 |
| 0027 | Aged Control | 16.9 | 15.6 | 13.8 | 12.9 | 13.2 | 11.2 | 133.5 |
| 0040 | Aged Control | 7.7 | 9.0 | 6.2 | 12.1 | 6.6 | 5.0 | 151.3 |
| 0049 | Aged Control | 0.6 | 3.6 | 2.3 | 13.0 | 3.4 | 0.0 | 172.7 |
| 0059 | Aged Control | 5.5 | 10.4 | 15.2 | 13.5 | 10.0 | 6.7 | 126.7 |
| 0067 | Aged Control | 13.4 | 14.0 | 19.5 | 14.3 | 11.1 | 7.0 | 139.1 |
| 0070 | Aged Control | 12.5 | 10.8 | 10.5 | 17.9 | 16.0 | 12.4 | 178.9 |
| 0650 | Aged Control | 0.3 | 4.9 | 0.0 | 7.9 | 0.3 | 0.0 | 125.8 |
| 2146 | Aged Control | 14.9 | 16.2 | 12.9 | 17.7 | 12.7 | 12.7 | 198.2 |
| 2367 | Aged Control | 3.7 | 4.3 | 5.7 | 4.6 | 3.7 | 2.7 | 44.7 |
| 2491 | Aged Control | 10.2 | 13.5 | 17.2 | 13.7 | 10.0 | 5.0 | 142.9 |

TABLE 11

PART D

Mutant Allele Frequencies at AD-Associated Loci in Cytochrome c Oxidase Subunit 1 & 2 Genes

| Patient | Diagnosis | COX1:155 | COX1:194 | COX1:415 | COX2:22 | COX2:95 | COX2:146 | Fisher Score |
|---|---|---|---|---|---|---|---|---|
| 2495 | Aged Contol | 5.1 | 2.6 | 2.1 | 7.5 | 10.2 | 5.8 | 64.1 |
| 2496 | Aged Contol | 5.3 | 3.3 | 2.4 | 10.1 | 8.3 | 7.1 | 103.2 |
| 2507 | Aged Contol | 18.4 | 20.6 | 11.1 | 20.1 | 13.7 | 15.8 | 245.6 |
| 2508 | Aged Contol | 23.9 | 15.8 | 13.2 | 25.6 | 21.7 | 22.2 | 260.3 |
| 2511 | Aged Contol | 12.4 | 13.3 | 10.0 | 14.5 | 8.6 | 14.9 | 158.2 |
| 2611 | Aged Contol | 15.7 | 14.5 | 12.7 | 18.9 | 15.6 | 11.9 | 203.4 |
| 2628 | Aged Contol | 11.4 | 20.8 | 7.2 | 16.8 | 8.9 | 9.6 | 240.2 |
| 35132 | Aged Contol | 9.3 | 4.4 | 7.9 | 18.0 | 17.9 | 12.1 | 157.6 |
| 447 | Aged Contol | 15.1 | 8.4 | 10.1 | 12.1 | 16.0 | 12.2 | 95.9 |
| 590 | Aged Contol | 14.9 | 25.1 | 15.0 | 26.0 | 15.1 | 19.4 | 310.9 |
| 591 | Aged Contol | 21.6 | 24.7 | 14.3 | 28.1 | 21.7 | 24.1 | 315.7 |
| 650 | Aged Contol | 12.4 | 20.0 | 13.8 | 25.7 | 18.0 | 17.4 | 287.9 |
| 808 | Aged Contol | 1.5 | 6.1 | 0.8 | 17.3 | 2.8 | 0.7 | 246.8 |
| 847 | Aged Contol | 17.9 | 10.8 | 9.3 | 20.3 | 10.7 | 11.6 | 237.9 |
| 1042 | Aged Contol | 25.9 | 17.6 | 19.8 | 26.0 | 21.5 | 19.4 | 259.4 |
| 1171 | Aged Contol | 21.1 | 18.6 | 15.3 | 20.6 | 21.2 | 15.0 | 214.2 |
| 327 | Aged Contol | 20.7 | 24.3 | 13.2 | 18.5 | 19.1 | 19.4 | 208.1 |
| 330 | Aged Contol | 31.5 | 31.5 | 26.9 | 31.9 | 26.4 | 25.2 | 242.2 |
| 332 | Aged Contol | 28.7 | 32.3 | 25.9 | 32.4 | 31.8 | 31.1 | 320.6 |
| 333 | Aged Contol | 9.1 | 7.3 | 8.9 | 24.7 | 22.7 | 18.7 | 223.5 |
| 335 | Aged Contol | 15.3 | 9.2 | 12.1 | 16.3 | 13.4 | 8.6 | 165.7 |
| 339 | Aged Contol | 12.0 | 11.1 | 10.1 | 19.6 | 16.7 | 14.3 | 196.3 |
| 341 | Aged Contol | 10.2 | 8.7 | 9.6 | 17.3 | 9.7 | 3.5 | 205.9 |
| 342 | Aged Contol | 14.4 | 16.9 | 13.9 | 20.0 | 20.2 | 16.1 | 167.8 |
| 344 | Aged Contol | 12.1 | 11.5 | 11.9 | 19.6 | 16.2 | 11.9 | 200.1 |
| 345 | Aged Contol | 7.2 | 9.3 | 6.7 | 12.2 | 10.4 | 9.8 | 127.2 |
| 346 | Aged Contol | 5.9 | 8.3 | 5.1 | 11.9 | 7.3 | 5.4 | 145.1 |

TABLE 11

PART E

Mutant Allele Frequencies at AD-Associated Loci in Cytochrome c Oxidase Subunit 1 & 2 Genes

| Patient | Diagnosis | COX1:155 | COX1:194 | COX1:415 | COX2:22 | COX2:95 | COX2:146 | Fisher Score |
|---|---|---|---|---|---|---|---|---|
| 350 | Aged Control | 7.4 | 9.5 | 6.5 | 12.9 | 4.9 | 4.9 | 168.1 |
| 354 | Aged Contol | 11.3 | 13.9 | 11.0 | 11.3 | 9.4 | 9.6 | 124.7 |
| 355 | Aged Contol | 12.4 | 11.0 | 10.3 | 11.7 | 10.5 | 10.4 | 116.9 |
| 449 | CBG | 23.3 | 18.7 | 16.4 | 21.6 | 16.7 | 19.6 | 226.4 |
| 502 | CBG | 14.9 | 8.7 | 14.5 | 18.8 | 12.2 | 9.0 | 191.5 |
| 236 | NIDDM | 8.5 | 11.5 | 9.1 | 10.3 | 11.3 | 14.0 | 88.3 |
| 248 | NIDDM | 13.5 | 12.2 | 9.8 | 13.6 | 9.6 | 13.0 | 145.0 |
| 257 | NIDDM | 7.6 | 10.0 | 9.3 | 12.3 | 10.5 | 13.4 | 111.7 |
| 258 | NIDDM | 2.1 | 6.7 | 7.2 | 12.9 | 6.7 | 8.8 | 132.8 |
| 270 | NIDDM | 8.2 | 12.1 | 9.4 | 10.1 | 13.6 | 13.6 | 80.8 |
| 271 | NIDDM | 8.4 | 12.0 | 10.7 | 8.8 | 17.6 | 17.4 | 36.8 |
| 391 | NIDDM | 1.9 | 8.4 | 7.7 | 13.6 | 12.3 | 6.1 | 138.4 |
| 409 | NIDDM | 0.7 | 9.2 | 8.6 | 9.8 | 8.6 | 7.1 | 93.6 |
| 414 | NIDDM | 14.7 | 11.4 | 10.3 | 13.0 | 12.0 | 9.3 | 137.8 |
| 909 | NIDDM | 10.6 | 9.6 | 7.9 | 20.5 | 14.4 | 12.9 | 219.7 |
| 448 | Parkinson's | 4.3 | 4.0 | 4.8 | 11.2 | 7.0 | 9.6 | 107.2 |
| 663 | Parkinson's | 21.8 | 17.9 | 9.1 | 22.7 | 17.2 | 21.4 | 255.4 |
| 1033 | Parkinson's | 21.2 | 22.3 | 15.6 | 26.4 | 17.3 | 12.2 | 324.7 |
| 1035 | Parkinson's | 8.2 | 10.0 | 4.8 | 15.2 | 11.6 | 26.7 | 127.5 |
| 1048 | Parkinson's | 17.9 | 19.3 | 14.8 | 20.4 | 20.1 | 16.3 | 211.9 |
| 1049 | Parkinson's | 15.7 | 11.8 | 13.4 | 20.4 | 16.0 | 12.2 | 210.1 |
| 1059 | Parkinson's | 7.1 | 11.4 | 11.3 | 17.1 | 16.1 | 9.2 | 170.1 |
| 1109 | Parkinson's | 14.5 | 14.0 | 11.4 | 18.7 | 12.2 | 10.0 | 217.9 |
| 1122 | Parkinson's | 11.5 | 9.1 | 8.8 | 17.4 | 12.7 | 41.3 | 98.4 |
| 1123 | Parkinson's | 2.3 | 3.7 | 3.3 | 8.6 | 5.1 | 2.5 | 99.1 |
| 1134 | Parkinson's | 15.7 | 10.6 | 10.0 | 14.9 | 16.5 | 10.0 | 148.1 |

TABLE 11

PART F

Mutant Allele Frequencies at AD-Associated Loci in Cytochrome c Oxidase Subunit 1 & 2 Genes

| Patient | Diagnosis | COX1:155 | COX1:194 | COX1:415 | COX2:22 | COX2:95 | COX2:146 | Fisher Score |
|---|---|---|---|---|---|---|---|---|
| 1162 | Parkinson's | 20.9 | 19.8 | 17.5 | 19.0 | 19.1 | 16.5 | 190.6 |
| 1175 | Parkinson's | 21.1 | 17.0 | 15.8 | 17.8 | 21.0 | 15.3 | 168.1 |
| 1184 | Parkinson's | 10.0 | 15.1 | 13.1 | 28.1 | 17.1 | 15.4 | 310.5 |
| 1204 | Parkinson's | 13.3 | 10.2 | 11.3 | 17.9 | 15.9 | 17.9 | 159.2 |
| 1211 | Parkinson's | 0.0 | 3.6 | 0.0 | 15.8 | 13.8 | 5.6 | 174.0 |
| 382 | Picks | 13.7 | 14.5 | 10.6 | 17.5 | 14.0 | 11.9 | 195.6 |
| 386 | Picks | 8.4 | 13.5 | 6.4 | 17.4 | 8.8 | 7.1 | 227.6 |

Neurologic Disease Controls: Parkinson's Disease, Pick's disease, Coritco-Basal Ganglionic Degneration (CBG);
Metabolic Disease Controls: Non-Insulin Dependent Diabetes Mellitus (NIDDM)

Thus, an improved mtDNA extraction procedure from buffy coat fractions of whole blood is described which provides DNA in which the relative proportion of mutant to normal mitochondrial alleles is selectively increased. Using a multiplexed primer extension assay and statistical analysis, we demonstrate that there are quantitative differences in the abundance of mutant alleles at each of several linked loci between sporadic Alzheimer's disease patients and controls.

Accordingly, an optimal procedure for extraction of mitochondrial DNA for use in a clinical DNA diagnostic assay for the detection of rare and multiple mutations in mitochondria encoded genes which segregate with mitochondria-associated disease has been demonstrated. The DNA extraction procedure meets the following criteria: (1) it is reproducible in the efficient isolation of mutant mtDNA (2) it provides a suitable DNA template for PCR amplification and (3) it is be amenable for high throughput automated DNA extraction.

In another aspect of the invention, there is provided a kit which contains supplies and reagents for isolating a complete population of mtDNA alleles from whole blood of a subject. The kit may contain, for example, solution for separation of mtDNA from whole cells, storage solution, wash solution, boiling solution, and combinations thereof, as well as any other solution useful in the isolation of mtDNA as described herein above.

The mtDNA separation solution preferably contains about ten parts of a 33.9% solution of sodium diatrizoate (density of about 1.20 gm/ml) and about 24 parts of a 9% ficoll solution, and is adjusted to a density of about 1.077 gm/ml.

Preferably, the isolation of white blood cells (buffy coat) is accomplished by centrifugation of whole blood through a cushion of the buffer. The erythrocytes and granulocytes sediment to the bottom of the tube, while lymphocytes and other mononuclear cells, i.e., monocytes together with platelets, remain at the plasma/buffer interphase.

The storage solution in which collected mononuclear cells may be resuspended and stored preferably contains about 0.9% NaCl and 1 mM EDTA.

The wash solution is preferably phosphate buffered saline, and the boiling solution is, generally, sterile water.

The kit may also include any container(s) for collecting blood and separating mtDNA therefrom. The solutions and/or containers may be sterilized by any known procedure.

EXAMPLES

DNA Isolation

Total cellular DNA is isolated by the procedures outlined below from fresh blood or from the frozen white blood cells prepared by the Accuspin procedure or the dextran procedure.

Blood was collected from two NIDDM patients and buffy coat was prepared by the dextran procedure. DNA was isolated from blood by the Proteinase K/SDS/phenol/chloroform procedure for blood (PSPC). DNA was isolated from buffy coat by the boiling procedure.

Extraction of DNA

The white blood cell/platelet fraction (buffy coat) in blood is prepared by several methods. In a first method, the buffy coat fraction is isolated by sedimentation of erythrocytes in a 10% dextran (MW 250,000) solution. In a second method, the buffy coat fraction is separated by centrifugation of whole blood in HISTOPAQUE® 1077-packed Accuspin™ tubes. In a third method, the buffy coat layer is isolated by low speed centrifugation of whole blood. DNA from the buffy coat fraction is extracted by (1) boiling procedure, or (2) proteinase K digestion followed by organic extraction. The extracted DNA is amplified by PCR and the products are analyzed for presence of AD-associated mutations. Our results reveal that the boiling procedure selectively increased the proportion of mutant to normal alleles at several mitochondria-disease associated loci, such as the loci associated with AD. Using a multiplexed primer extension assay, we demonstrate quantitative differences in the abundance of mutant alleles at each of these loci between Alzheimer's disease patients and controls.

White Blood Cell Isolation

Ten mL of blood are drawn and collected in vacutainers with yellow or purple stoppers (Beckton Dickinson; ACD solution, EDTA solution). The blood sample is then divided into two aliquots for two different white blood cell preparations.

Dextran procedure:

18 mL of dextran solution (3% dextran, average MW=250,000 kiloDaltons, 0.9% sodium chloride, 1 mM EDTA) is added to 6 mL of blood, mixed, and the mixture is maintained at room temperature for 40 min without agitation to allow erythrocytes to sediment. The plasma and white blood cell fraction (buffy coat) is transferred to a centrifuge tube and white blood cells are sedimented by centrifugation at 7,000 g for 10 min. The white cell pellet is resuspended in 3.6 mL of water and vortexed for 30 s to lyse the remaining erythrocytes. A 1.2 mL volume of a 0.6 M sodium chloride solution is added and the sample is centrifuged at 7,000 g for 10 min to sediment the white blood cells. The white cell pellet is resuspended in 0.4 mL of a solution containing 0.9% sodium chloride/1 mM EDTA and stored at −80° C.

Accuspin procedure (A):

Two mL of blood are processed using Accuspin™ Tubes (Sigma Diagnostics, St. Louis, Mo.) following the manufacturer's instructions. Thus, 3 mL of HISTOPAQUE® 1077 are added to the upper chamber of Accuspin™ Tube and the device is centrifuged at 1000 g for 30 s. The blood sample is then introduced into the upper chamber and separated by centrifugation at 1000 g for 10 min at room temperature. After centrifugation, the plasma and white blood cell layers (buffy coat) are transferred to a new tube and (a) are immediately frozen in the presence of 10% DMSO, or (b) the white blood cells are sedimented by centrifugation at 7,000 g for 10 min. The white cell pellet is resuspended in 0.4 mL of a solution containing 0.9% sodium chloride/1 mM EDTA and stored at −80° C.

Proteinase K/SDS/phenol/chloroform procedure for blood (PSPC):

Five mL of fresh blood is collected in an ACD or EDTA vacutainer and spun at 2,500 rpm for 10 min at 4° C. The white blood cells, which form an interphase between the red blood cell bottom layer and the plasma top layer, are removed and transferred to a centrifuge tube. The white cells are washed by addition of 5 mL of TE buffer (10 mM Tris-HCl, pH 7.5, 1 mM EDTA) and sedimented by centrifugation at 2,500 rpm for 10 min at 4° C. The white cell pellet is then resuspended in 5 mL of TE buffer containing 0.4 mL of 10% SDS and 0.1 mL of proteinase K (20 mg/mL). The sample is incubated at 37° C. for 4 h with continuous agitation at 200 rpm on an orbital shaker. The sample is extracted twice with an equal volume of equilibrated phenol (Gibco BRL) followed by two extractions with an equal volume of chloroform:isoamyl alcohol (24:1). During each extraction, the sample is mixed well, allowed to stand for 5 min, and then centrifuged at 5,700 rpm for 10 min at room temperature. The DNA is precipitated from the aqueous layer by the addition of 1/10 volume 3 M sodium acetate (pH 5) and 2 volumes of 100% ethyl alcohol. After incubation at −20° C. for 12 to 16 hours, the precipitated DNA is collected by centrifugation at 10,000 g for 20 min at 4° C. The DNA pellet is washed with 70% ethyl alcohol, air dried, then resuspended in 0.1–0.2 mL of TE buffer. The DNA concentration is determined by UV absorption at 260 nm. The DNA is stored at 4° C.

SDS/proteinase K/phenol-chloroform procedure for white blood cells (SPP):

Frozen white blood cells (0.2 mL) are thawed, pelleted, and washed twice with 0.6 mL of Dulbecco's Phosphate Buffered Saline as described above and then resuspended in 0.2 mL of 1% SDS. The cells are lysed by incubation in a boiling water bath for 10 min. After cooling to room temperature, 2 µL of a proteinase K solution (20 mg/mL) is added and the sample is incubated at 37° C. for 15 min. The samples are extracted twice with an equal volume of equilibrated phenol:chloroform:isoamyl alcohol (25:24:1), followed by two extractions with an equal volume of chloroform:isoamyl alcohol (24:1). In the extraction process, the sample is mixed well and then is centrifuged at 14,000 rpm for 10 min at room temperature. After the extractions are complete, the DNA is precipitated by the addition of 1/10 volume 5 M sodium chloride and 2 volumes of 100% ethyl alcohol. After incubation at −20° C. for 12 to 16 hours, the DNA is pelleted by centrifugation at 14,000 g for 20 min. The DNA pellet is washed with 70% ethyl alcohol, air dried, then resuspended in 0.1–0.2 mL of TE buffer. The DNA concentration is determined by UV absorption at 260 nm. The DNA is stored at 4° C.

Boiling procedure:

Frozen white blood cells (0.2 mL) are thawed and sedimented by centrifugation at 12,000 g for 5 min. The white cell pellet is washed twice with 0.6 mL of Dulbecco's Phosphate Buffered Saline (PBS; Gibco BRL, Life Technologies, Inc., Grand Island, N.Y.) and resuspended in 0.2 mL water. The cells are lysed by incubation in a boiling water bath for 10 min. After cooling to room temperature, the cellular debris is sedimented by centrifugation at 14,000 g for 2 min. The supernatant is transferred to a new vial and the DNA concentration is determined by UV absorption at 260 nm. The DNA sample is stored at about −80° C.

Oligonucleotide Synthesis

Oligonucleotides are synthesized on an Applied Biosystems 394 DNA/RNA synthesizer (Perkin Elmer) using standard phosphoramidite chemistry. 5' Fluorescein-labeled oligonucleotide primers are obtained by using the 6-FAM Amidite reagent (Perkin Elmer, Applied Biosystems Division) in the last step of the automated synthesis. Tritylated and fluorescein-labeled oligonucleotides are purified by reverse phase chromatography using an acetonitrile gradient in 0.1 M triethylammonium acetate, pH 6.8 running buffer. The purified oligonucleotides migrate as single bands on a 15% denaturing polyacrylamide gel and the fluorescein-labeled oligonucleotides migrate as a homogeneous product after electrophoresis on an Applied Biosystems Model 373 Sequencing System (Perkin Elmer, Applied Biosystems Division).

Preparation of Templates for Primer Extension Assay

PCR amplification of cellular DNA is carried out in a total volume of 50 µL using two sets each of COX1- and COX2-specific primers (Table 1). Thus, a 246 bp fragment of the COX1 gene containing the codons sites for amino acids 155, 193, and 194 is generated by using the first primer set (SEQ ID NO:1 and SEQ ID NO:2). A 200 bp fragment containing the codon for COX1 amino acid 415 is generated by using the second set of primers (SEQ ID NO:3 and SEQ ID NO:4). Similarly, two regions of the COX2 gene are amplified by PCR to generate DNA fragments 255 bp and 308 bp long, respectively (primer pairs with SEQ ID NO:5 and SEQ ID NO:6, and SEQ ID NO:7 and SEQ ID NO:8, respectively). The codons within the fragments are shown in Table 1. Typically, reactions contained ~1 µg of cellular DNA, 2.5 U of AmpliTaq® DNA polymerase (Perkin Elmer), 20 pmol each the forward primer and the reverse primer and 10 nmol of each dNTP in PCR buffer (10 mM Tris.HCl, pH 8.3, 50 mM KCl, 2 mM $MgCl_2$). After initial denaturation at 95° C. for 10 s in a Gene Amp PCR System 9600 thermal cycler (Perkin Elmer), the samples are amplified for 30 cycles under the following conditions: 95° C. for 1 min, 60° C. for 1 min, 72° C. for 1 min and final extension at 72° C. for 7 min. After amplification, the PCR products are analysed by electrophoresis on a 0.8% agarose gel.

PCR amplification of cellular target using UlTma™ DNA polymerase (Perkin Elmer) is carried out according to the manufacturer's instructions. Each reaction contains ~1 µg cellular DNA, 3 U of UlTma™ DNA polymerase, 20 pmol each the forward primer and the reverse primer and 1.25 nmol of each dNTP in Ultma™ buffer (10 mM Tris.HCl, pH 8.8, 10 mM KCl, 2 mM $MgCl_2$, 0.002% Tween 20® (v/v)). After initial denaturation at 95° C. for 10 s, the samples are amplified for 25 cycles under the following conditions: 95° C. for 1 min, 55° C. for 1 min, 72° C. for 1 min and final extension at 72° C. for 7 min.

Residual nucleotides after the PCR reaction are dephosphorylated by addition of 1 unit of calf intestine alkaline phosphatase (CAP) in 5 µL of 10X CAP buffer (100 mM Tris.HCl, pH 8.3, 10 mM $MgCl_2$, 10 mM $ZnCl_2$) to the PCR reaction mixture and incubation for 30 min at 37° C. in thermal cycler. Then 1.1 µL of 0.25 M EDTA, pH 8.0 is added and the alkaline phosphatase is denatured at 75° C. for 10 min.

Double-stranded PCR products are purified away from primers, nucleosides and enzymes using QIAquick™ columns (Qiagen, Inc.) following the recommended procedure of the manufacturer. Thus, 250 µL of buffer PB are added to the PCR reaction mixture and mixed. A QIAquick™ spin column is placed in a 2 mL collection tube and the sample is loaded. The sample is centrifuged for 30–60 s at 14000 g, and the flowthrough is discarded. The adsorbed PCR product is washed with 750 µL of buffer PE, and then eluted with 50 µL of 10 mM Tris.HCl, pH 8.5. The purified product solution is dried in a Savant SpeedVac Concentrator (Savant Instruments, Inc.) and then reconstituted in 20 µL of water.

Primer Extension Reactions

The fluorescein-labeled primers and nacleotide combinations for analysis of the AD-associated mutations are shown in Table 2. Stock solutions of each dNTP and ddNTP are prepared by mixing equimolar amounts of the nucleotides (United States Biochemical Corporation), with $MgCl_2$ and diluting the mixture to the desired concentration with TE. The primers are diluted in TE to provide final stock concentrations of 40 fmol/µL. One µL of the purified PCR-amplified DNA fragment is used as template for each assay. The primer extension reactions are performed in a total volume of 8 µL. The reaction mixes contained template, 20 fmol fluorescein-labeled primer, 400 mM ddNTPs/25 mM dNTPs of the appropriate nucleotide combination and 0.6 unit of UlTma™ DNA polymerase in buffer containing 10 mM Tris-HCl, pH 8.8, 10 mM KCl, 0.002% Tween 20, 2 mM $MgCl_2$. Each primer extension assay also includes primer (no template), homoplasmic wild-type and mutant DNA controls. After initial denaturation at 95° C. for 2 min, the reaction conditions comprise 20 cycles of 95° C. for 20 s and 55° C. for 40 s followed by indefinite hold at 4° C. when the cycles are completed. The samples are then concentrated to ~1 µL by incubating open reaction tubes at 94° C. for 7 min, followed by addition of 8 µL of loading dye (0.5% blue dextran in 83% formamide/8.3 mM EDTA, pH 8.0).

Polyacrylamide Gel Electrophoretic Analysis of Primer Extension Reaction Products The products of the primer extension reaction are analyzed on an ABI 373 Sequencer using a 12% denaturing polyacrylamide gel and Tris borate/EDTA as running buffer. During the gel pre-electrophoresis stage, the samples in loading dye are denatured for 3 min at 85° C. Three µL aliquots of the standards (primer, homoplasmic wild-type and mutant DNA) and each unknown reaction mixture are then loaded and electrophoresed according the manufacturer's instructions. Quantitative heteroplasmy analysis is carried out by estimating the fluorescence band intensities associated with the wild-type and mutant DNA-derived extension products using GENESCAN™ 672 software (Perkin Elmer, Applied Biosystems Division) and correlating the values with the homoplasmic wild-type and mutant DNA controls.

PCR Amplification of Cytochrome c Oxidase Genes for Cloning/Sequencing

Mitochondria-encoded cytochrome c oxidase subunits 1 and 2 gene sequences are amplified by the polymerase chain reaction. Primer design is based on the published mitochondrial DNA sequence (Anderson et al, (1981) Nature 290: 457–465) (Table 3). The primers are located 25–40 bp upstream and downstream of the gene coding regions and within the coding regions, and primer pairs are chosen to provide PCR products ranging in length between 280–341 base pairs. PCR is performed in four independent reactions in order to dilute any reading error introduced by the Taq polymerase. The total reaction volume is 50 µL, and contained ~1 µg of total cellular DNA, 200 ng each of the appropriate forward and reverse primers, 200 µM for each dNTP (dATP, dGTP, dCTP, dTTP), 10 mM Tris-HCl, pH 8.3, 50 mM KCl, 2 mM $MgCl_2$ and 1 unit of Taq polymerase (AmpliTaq, Perkin-Elmer/Applied Biosystems, Foster City). After initial denaturation at 95° C. for 10 s, the reaction comprised 25 cycles at 95° C. for 1 min, 60° C. for 1 min, and 72° C. for 1 min, followed by 72° C. for 4 min and cooling to 4° C. Presence of PCR product in the reactions for each COX gene is verified by removal of 5 µL from each tube and analysis by horizontal agarose gel electrophoresis. The PCR products from the reactions are pooled, isolated by ethanol/NaOAc precipitation and resuspended in 40 µL of TE buffer.

PCR Amplification of tRNA Lysine and ATP Synthase Subunit 8 Genes for Cloning/Sequencing Mitochondria-encoded tRNA lysine and ATP Synthase subunit 8 sequences were amplified by polymerase chain reaction. Primers were designed according to the published human mtDNA sequence (Andersen et al., (1981) *Nature* 290: 457–465). Forward primers were located at the 5'-end inside the tRNA lysine gene (nucleotide position 8311–8336; 5'-TAGCATTAACCTTTTAAGTTAAAGA-3'; SEQ ID NO: 42) and at the 3'-end of the ATP synthase subunit 8 gene (nucleotide position 8516–8535; 5'-TCGTTCATTTTGGTTCTCA-3'; SEQ ID NO: 43).

PCR is performed as described, except for the temperature profile, which is 25 cycles at 95° C. for 1 min, 50° C. for 1 min, and 72° C. for 1 min, followed by 72° C. for 4 min and cooling to 4° C. PCR product is purified by preparative horizontal agarose gel electrophoresis and ligated with the pCRII TA cloning vector (Invitrogen, San Diego), according to manufacturer's instructions. Ligatins are transformed into competnet *E. coli* XL1BlueMRF' cells (Stratagene, San Diego) according to manufacturer's instructions. Recombinant clones are identified by blue/white color selection and DNA for sequencing is prepared using the Qiagen 96well Plasmid kit (Qiagen, Chatsworth).

Sequence analysis is performed for 50 clones per patient using dye terminator cycle sequencing chemistry provided by the PRISM Cycle Sequencing Kit (Perkin Elmer, Foster City). Sequences are analyzed using the 373A automated DNA sequencer (ABI, Foster City) and the Sequence Navigator software package (ABI, Foster City). All sequences are analyzed by comparing to the published human mtDNA sequence (Anderson et al., (1981) *Nature* 290: 457–465) and mutations are noted.

Purification of the PCR products, Cloning and Screening

The PCR products are electrophoresed on preparative horizontal agarose gels. The PCR product bands are excised from the gel, minced, placed into 0.3 mL of 1 M NaCl, and frozen at −80° C. until solid. The agarose pieces are incubated at 45° C. for 20 min in order to elute the DNA. Agarose pieces are centrifuged to the bottom of the vials and the supernatants are transferred to new vials. The PCR products are ethanol precipitated, pelleted by centrifugation, air-dried, and resuspended in 20 µL of TE buffer.

The PCR products are directly ligated into the vector PCRII supplied with the TA-Cloning kit (Invitrogen, San Diego, Calif.). The vector pCRII contains the lacZ gene surrounding the cloning site for blue/white colony selection and confers resistance to ampicillin and kanamycin. The ligation reaction contained 4–7 µL of PCR product, 50 ng of vector, 1 µL of 10× ligation buffer provided with the kit, 1 µL T4 DNA ligase and supplemented with water to provide a final reaction volume of 11 µL. Ligation reactions are incubated overnight at 11–12° C. Competent *E. coli* XL1 Blue MRF' cells or XL2 Blue MRF' cells (Stratagene, San Diego, Calif.) are transformed with 3–4 µL of ligation product using 100 µL of competent cells in the presence of 1.7 µL β-mercaptoethanol. After a 30 min incubation on ice, the cells are heat shocked at 42° C. for 1 min, placed on ice for 2 min, diluted with 0.9 mL of SOC medium, and incubated at 37° C. for 1 hour with shaking at 225 rpm. One hundred µL of the transformation is spread onto SOB agar plates containing 50 mg/ml of ampicillin, 50 mg/ml of kanamycin, 100 µg/mL of X-gal, and 20 µg/mL of IPTG (for blue/white color selection). Plates are incubated overnight at 37° C.

Purification of Sequencing Templates

White colonies indicating recombinant clones are selected and grown for 24 hours at 37° C. in 30–50 ml of SOB containing 50 µg/ml ampicillin and 50 µg/ml kanamycin. The cells are pelleted by centrifugation. The plasmid DNA is purified using the Qiagen Plasmid Kit (Qiagen, Chatsworth, Calif.). The DNA is resuspended in 100 µl of sterile water and its concentration is determined by $A_{260}$ absorbance.

Dye Terminator Cycle Sequencing

Sequencing reactions are performed using the PRISM Ready Reaction DyeDeoxy Terminator Cycle Sequencing Kit (Applied Biosystems, Foster City, Calif.) followed by sequence analysis on the Applied Biosystems Model 373A DNA sequencing system. The reaction mixtures are in a final volume of 20 µL and contain kit-included terminator premix (dATP, dCTP, dTTP, dGTP, A-dyedeoxy, T-dideoxy, G-dideoxy, C-dideoxy, Tris-HCl, pH 9.0, ammonium sulfate, magnesium chloride, AmpliTaq DNA polymerase), template DNA as prepared by the procedure described above, and sequencing primer (M13 Forward or M13 Reverse primers). Thermal cycling in the PE9600 thermal cycler is performed as follows: 98° C. for 20 s, 30 cycles of 96° C. for 20 s, 44° C. for 10 s, and 60° C. for 4 min, followed by cooling to 4° C. Excess dideoxy terminators are removed using CentriSep spin columns (Princeton Separations, New Jersey). The purified sequencing reactions are dried in a vacuum centrifuge, resuspended in 3.5 µL of loading dye (8 mM EDTA, pH 8.0, 0.5% blue dextran, 80% formamide), denatured by heating, and loaded onto an Applied Biosystems 373A DNA sequencer.

Sequence Analysis and Determination of Point Mutations

All sequence data output from the Applied Biosystems 373A sequencer are compared with the published Cambridge sequence and our previously obtained sequencing data. The analysis is carried out using the Applied Biosystems 373A Sequence Data Analysis Software and the Sequence Navigator Software. Mutations in the sequences are identified, marked, their locations computed and amino acid substitutions are determined. Further analysis compares data between patients in order to identify common mutations associated with AD patients and not with controls.

Follow-up Treatment of DNA Extracted from Buffy Coat Fraction by the Boiling Procedure A crude DNA preparation obtained by boiling the buffy coat of a blood sample is aliquoted into nine fractions (~8 µg each) and further purified by the following procedures. The resulting DNA isolates are then amplified by PCR and interrogated for the presence of the AD-associated mutations in order to assess whether the purification protocols preserved the mutant alleles in the sample.

(a) A DNA fraction is treated with 1/10 volume of 3M sodium acetate (pH 5.0) and 2× volumes of 100% ethanol. After incubation at −20° C. overnight, the DNA is precipitated by centrifugation, washed with 70% ethanol, air dried, and resuspended in 10 µL of water.

(b) A DNA fraction is extracted two times with phenol, two times with chloroform and then precipitated with ethanol as in (A). The DNA pellet is washed with 70% ethanol, air dried, and resuspended in 10 µL of water.

(c) A DNA fraction is incubated in the presence of 1% SDS and 400 µg/ml proteinase K for 4 hours at 37° C. The DNA is extracted twice with phenol, twice with chloroform and ethanol precipitated. The DNA pellet is washed with 70% ethanol, air dried, and resuspended in 10 μL of water.

(d) A DNA fraction is incubated in the presence of 1% SDS and 400 μg/ml proteinase K for 4 hours at 37° C. The sample is incubated in a boiling waterbath for 10 min to inactivate the proteinase K. The DNA is diluted with 250 μL of TE buffer and subjected to ultrafiltration using a Microcon-100 microconcentrator (MW cutoff 100,000 daltons, Amicon, Beverly, Mass.) following the manufacturer's instructions.

(e) A DNA fraction is treated with 10 mM NaOH, pH 12, for 30 min at room temperature. The DNA is then extracted two times with phenol, two times with chloroform and ethanol precipitated. The DNA pellet is washed with 70% ethanol, air dried, and resuspended in 10 μL of water.

(f) A DNA fraction is treated with 0.12 M sodium acetate, pH 5.0, for 30 min at room temperature. The DNA is then extracted two times with phenol, two times with chloroform and ethanol precipitated. The DNA pellet is washed with 70% ethanol, air dried and resuspended in 10 μL of water.

(g) The DNA is treated with 4 M guanidinium isothiocyanate, 25 mM sodium acetate, pH 5.0, 0.5% sapcosyl, 0.1 M β-mercaptoethanol, for 30 min at room temperature. Then the DNA solution is diluted twn-fold with TE and desalted using a Centricon-100 ultrafiltration concentrator. Following two washes with 250 μL of TE, the retentate containing the purified DNA is recovered.

We claim:

1. A method for determining the presence or risk of mitochonidrial-associated disease comprising:
   a) boiling a crude buffy coat fraction from a whole blood sample in water to lyse cells of the buffy coat fraction, thereby extracting cellular DNA from the lysed cells, in the absence of a mixture of SDS and Proteinase K, a mixture of phenol and chloroform or both; and
   b) analyzing the extracted cellular DNA for mutations in a mitochondrial gene at one or more loci that correlate with mitochondrial-associated disease, and therefrom determining the presence or risk of mitochondrial-associated disease.

2. The method of claim 1, further comprising
   separating the crude buffy coat from erythrocytes by sedimentation.

3. The method of claim 1, wherein said crude buffy coat is boiled for about 5 to 20 minutes.

4. The method of claim 1, wherein said crude buffy coat is boiled for about 10 minutes.

5. The method of claim 1 wherein the mitochondrial-associated disease is Alzheimer's disease.

6. The method of claim 5 wherein the extracted DNA is analyzed for mutations at one or more of six genetic loci selected from the group consisting of COX1 codon 155, COX1 codon 194, COX1 codon 415, COX2 codon 22, COX2 codon 95 and COX2 codon 146.

7. The method of claim 6 wherein analysis of the DNA comprises determining the mutational burden at said six loci by Fisher score analysis.

8. The method of claim 1 wherein the mitochondrially-associated disease is non-insulin dependent diabetes mellitus.

9. The method of claim 8 wherein the cellular DNA is analyzed for mutations in one or more loci in an ATP synthase subunit 8 gene.

10. The method of claim 9 wherein analysis of the cellular DNA comprises determining the mutational burden at genetic loci in the ATP synthase subunit 8 gene and tRNA lysine gene.

11. The method of claim 1, further comprising amplifying said extracted cellular DNA to provide amplified DNA.

12. The method of claim 11 wherein the extracted cellular DNA is amplified by polymerase chain reaction (PCR) or a transcriptional amplification system.

13. The method according to claim 12 wherein the transcriptionial amplification system is a self-sustained sequence replication system.

14. The method of claim 12 wherein the extracted cellular DNA is amplified by PCR.

15. The method of claim 11 wherein the amplified cellular DNA is analyzed for said mutations to determine the level of heteroplasmy.

16. The method of claim 11 wherein the amplified cellular DNA is analyzed by hybridization analysis after amplification.

17. The method of claim 15 wherein the amplified cellular DNA is analyzed by oligonucleotide ligation assay.

18. The method of claim 15, wherein the amplified cellular DNA is analyzed for said mutations using a primer extension assay.

19. The method of claim 1, further comprising quantifying the degree of heteroplasmy at said one or more loci to determine mutational burden at each of said loci and total mutational burden for all of said loci.

20. The method of claim 19 wherein the overall mutational burden is determined by multivariate discriminant analysis techniques.

21. The method of claim 20 wherein the mutational burden is determined by Fisher score method of discrimination analysis.

22. The method of claim 8 wherein the cellular DNA is analyzed for mutations in one or more loci in a tRNA lysine gene.

23. The method of claim 8 wherein the cellular DNA is analyzed for mutations in one or more loci in an ATP synthase 8 gene and a tRNA lysine gene.

* * * * *

UNITED STATES PATENT AND TRADEMARK OFFICE
CERTIFICATE OF CORRECTION

PATENT NO : 6,027,883
DATED : Feb. 22, 2000
INVENTOR(S) : Corrina Herrnstadt, et al.

It is certified that error appears in the above-identified patent and that said Letters Patent are hereby corrected as shown below:

Claim 1, column 51, line 57, "mitochonidrial-associated" should read --mitochondrial-associated--.

Signed and Sealed this

Eighth Day of May, 2001

Attest:

NICHOLAS P. GODICI

*Attesting Officer*    *Acting Director of the United States Patent and Trademark Office*

```
                        SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
           (A) LENGTH: 24 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:1:

GAGCCTCCGT AGACCTAACC ATCT                                              24

(2) INFORMATION FOR SEQ ID NO:2:

(i) SEQUENCE CHARACTERISTICS:
           (A) LENGTH: 22 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:2:

GGTCGAAGAA GGTGGTGTTG AG                                                22

(2) INFORMATION FOR SEQ ID NO:3:

(i) SEQUENCE CHARACTERISTICS:
           (A) LENGTH: 25 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:3:

CCATCATAGG AGGCTTCATT CACTG                                             25

(2) INFORMATION FOR SEQ ID NO:4:

(i) SEQUENCE CHARACTERISTICS:
           (A) LENGTH: 27 base pairs
           (B) TYPE: nucleic acid
```

```
        (C) STRANDEDNESS: double
        (D) TOPOLOGY: linear (ii) MOLECULE TYPE: DNA (genomic)

(xi) SEQUENCE DESCRIPTION: SEQ ID NO:4:

TGATAGGATG TTTCATGTGG TGTATGC                                        27

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

CATGCAGCGC AAGTAGGTCT ACAAGAC                                        27

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

TGTTATGTAA AGGATGCGTA GGGATGG                                        27

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

CCTGCCCGCC ATCATCCTAG T                                              21

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

AGCCTAATGT GGGGACAGCT CATG                                           24

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: double
        (D) TOPOLOGY: linear
```

(ii) MOLECULE TYPE: DNA (genomic)

(xi) SEQUENCE DESCRIPTION: SEQ ID NO:9:

TGGCCCCTAA GATAGAGGAG A                                             21

(2) INFORMATION FOR SEQ ID NO:10:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:10:

GACTGGGAGA GATAGGAGAA GTAGG                                         25

(2) INFORMATION FOR SEQ ID NO:11:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:11:

AGGACTGGGA GAGATAGGAG AAGTA                                         25

(2) INFORMATION FOR SEQ ID NO:12:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:12:

ACCTACGCCA AAATCCATTT C                                             21

(2) INFORMATION FOR SEQ ID NO:13:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:13:

TCCCCTATCA TAGAAGAGCT TATCA                                         25

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:14:

GACTAGGATG ATGGCGGGCA                                                  20

(2) INFORMATION FOR SEQ ID NO:15:

(i) SEQUENCE CHARACTERISTICS:
            (A) LENGTH: 16 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:15:

GGGAGGGCGA TGAGGA                                                      16

(2) INFORMATION FOR SEQ ID NO:16:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:16:

CGCATCCTTT ACATAACAGA CGAG                                             24

(2) INFORMATION FOR SEQ ID NO:17:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:17:

GGCCAATTGA TTTGATGGTA                                                  20

(2) INFORMATION FOR SEQ ID NO:18:

(i) SEQUENCE CHARACTERISTICS:
            (A) LENGTH: 21 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:18:

GGCCAATTGA TTTGATGGTA A                                                21

(2) INFORMATION FOR SEQ ID NO:19:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:19:

CACCAATGGT ACTGAACCTA CGAG                                              24

(2) INFORMATION FOR SEQ ID NO:20:

(i) SEQUENCE CHARACTERISTICS:
         (A) LENGTH: 24 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:20:

ATTATTATAC GAATGGGGGC TTCA                                              24

(2) INFORMATION FOR SEQ ID NO:21:

(i) SEQUENCE CHARACTERISTICS:
         (A) LENGTH: 24 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:21:

TTATTATACG AATGGGGGCT TCAA                                              24

(2) INFORMATION FOR SEQ ID NO:22:

(i) SEQUENCE CHARACTERISTICS:
         (A) LENGTH: 22 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:22:

CTGATCCGTC CTAATCACAG CA                                                22

(2) INFORMATION FOR SEQ ID NO:23:

(i) SEQUENCE CHARACTERISTICS:
         (A) LENGTH: 24 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:23:

AGGGCGTGAT CATGAAAGGT GATA                                              24

(2) INFORMATION FOR SEQ ID NO:24:

(i) SEQUENCE CHARACTERISTICS:
         (A) LENGTH: 21 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:24:

GTCCAATGCT TCACTCAGCC A                                              21

(2) INFORMATION FOR SEQ ID NO:25:

(i) SEQUENCE CHARACTERISTICS:
             (A) LENGTH: 18 base pairs
             (B) TYPE: nucleic acid
             (C) STRANDEDNESS: double
             (D) TOPOLOGY: linear (ii) MOLECULE TYPE: DNA (genomic)

(xi) SEQUENCE DESCRIPTION: SEQ ID NO:25:

TATGCGGGGA AACGCCAT                                                  18

(2) INFORMATION FOR SEQ ID NO:26:

(i) SEQUENCE CHARACTERISTICS:
             (A) LENGTH: 21 base pairs
             (B) TYPE: nucleic acid
             (C) STRANDEDNESS: double
             (D) TOPOLOGY: linear (ii) MOLECULE TYPE: DNA (genomic)

(xi) SEQUENCE DESCRIPTION: SEQ ID NO:26:

GGCAACTGAC TAGTTCCCCT A                                              21

(2) INFORMATION FOR SEQ ID NO:27:

(i) SEQUENCE CHARACTERISTICS:
             (A) LENGTH: 21 base pairs
             (B) TYPE: nucleic acid
             (C) STRANDEDNESS: double
             (D) TOPOLOGY: linear (ii) MOLECULE TYPE: DNA (genomic)

(xi) SEQUENCE DESCRIPTION: SEQ ID NO:27:

GTTTGGTATT GGGTTATGGC A                                              21

(2) INFORMATION FOR SEQ ID NO:28:

(i) SEQUENCE CHARACTERISTICS:
             (A) LENGTH: 20 base pairs
             (B) TYPE: nucleic acid
             (C) STRANDEDNESS: double
             (D) TOPOLOGY: linear (ii) MOLECULE TYPE: DNA (genomic)

(xi) SEQUENCE DESCRIPTION: SEQ ID NO:28:

GGCCATCAAT TTCATCACAA                                                20

(2) INFORMATION FOR SEQ ID NO:29:

(i) SEQUENCE CHARACTERISTICS:
             (A) LENGTH: 24 base pairs
             (B) TYPE: nucleic acid
             (C) STRANDEDNESS: double
             (D) TOPOLOGY: linear (ii) MOLECULE TYPE: DNA (genomic)

(xi) SEQUENCE DESCRIPTION: SEQ ID NO:29:

ATACCTATGT ATCCAATTGG TTCT                                                  24

(2) INFORMATION FOR SEQ ID NO:30:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:30:

GGAATAATCT CCCATATTGT AACT                                                  24

(2) INFORMATION FOR SEQ ID NO:31:

(i) SEQUENCE CHARACTERISTICS:
            (A) LENGTH: 18 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:31:

CAGGCCACCT ACGGTGAA                                                         18

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:32:

AGTGCTCTGA GCCCTAGGAT                                                       20

(2) INFORMATION FOR SEQ ID NO:33:

(i) SEQUENCE CHARACTERISTICS:
            (A) LENGTH: 19 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:33:

ATTCCGGATA GGCCCGAGA                                                        19

(2) INFORMATION FOR SEQ ID NO:34:

(i) SEQUENCE CHARACTERISTICS:
            (A) LENGTH: 22 base pairs
            (B) TYPE: nucleic acid
            (C) STRANDEDNESS: double
            (D) TOPOLOGY: linear -continued (ii) MOLECULE TYPE: DNA (genomic)

(xi) SEQUENCE DESCRIPTION: SEQ ID NO:34:

TCGGCGTAAA TCTAAGTTTC TT                                                 22

(2) INFORMATION FOR SEQ ID NO:35:

(i) SEQUENCE CHARACTERISTICS:
           (A) LENGTH: 19 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:35:

GGGGTTCGAT TCCTTCCTT                                                     19

(2) INFORMATION FOR SEQ ID NO:36:

(i) SEQUENCE CHARACTERISTICS:
           (A) LENGTH: 24 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:36:

TCGTCAAAGT TAAATTATAG GCTA                                               24

(2) INFORMATION FOR SEQ ID NO:37:

(i) SEQUENCE CHARACTERISTICS:
           (A) LENGTH: 23 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:37:

ACCTCGTCTG TTATGTAAAG GAT                                                23

(2) INFORMATION FOR SEQ ID NO:38:

(i) SEQUENCE CHARACTERISTICS:
           (A) LENGTH: 20 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:38:

CGCCATCATC CTAGTCCTCA                                                    20

(2) INFORMATION FOR SEQ ID NO:39:

(i) SEQUENCE CHARACTERISTICS:
           (A) LENGTH: 23 base pairs
           (B) TYPE: nucleic acid
           (C) STRANDEDNESS: double
           (D) TOPOLOGY: linear

```
        (ii) MOLECULE TYPE: DNA (genomic)

(xi) SEQUENCE DESCRIPTION: SEQ ID NO:39:

ATGAGTGCAA GACGTCTTGT GAT                                               23

(2) INFORMATION FOR SEQ ID NO:40:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:40:

AATCGAGTAG TACTCCCGAT TGA                                               23

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:41:

GTTAGCTTTA CAGTGGGCTC TAGA                                              24

(2) INFORMATION FOR SEQ ID NO:42:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:42:

TAGCATTAAC CTTTTAAGTT AAAGA                                             25

(2) INFORMATION FOR SEQ ID NO:43:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:43:

TCGTTCATTT TGGTTCTCA                                                    19
```